US010405839B2

(12) United States Patent
Thomas et al.

(10) Patent No.: US 10,405,839 B2
(45) Date of Patent: Sep. 10, 2019

(54) ORGANIC SPECIMEN ORIENTATION, SEGMENTATION AND RETRIEVAL DEVICE

(71) Applicant: Altor Health LLC, Salt Lake City, UT (US)

(72) Inventors: Andrew Thomas, Alpine, UT (US); Samuel Crandall Thomas, Salt Lake City, UT (US); Benjamin Reed Fogg, Salt Lake City, UT (US); Joseph Bradley Fogg, Bountiful, UT (US)

(73) Assignee: Altor Health LLC, Salt Lake City, UT (US)

(*) Notice: Subject to any disclaimer, the term of this patent is extended or adjusted under 35 U.S.C. 154(b) by 291 days.

(21) Appl. No.: 15/094,742

(22) Filed: Apr. 8, 2016

(65) Prior Publication Data

US 2016/0296244 A1 Oct. 13, 2016

Related U.S. Application Data

(60) Provisional application No. 62/144,493, filed on Apr. 8, 2015.

(51) Int. Cl.
*A61B 17/00* (2006.01)
*A61B 17/3205* (2006.01)

(52) U.S. Cl.
CPC .. *A61B 17/00234* (2013.01); *A61B 17/32056* (2013.01); *A61B 2017/00287* (2013.01)

(58) Field of Classification Search
CPC ........ A61B 17/00234; A61B 17/32056; A61B 2017/00287; A61B 17/221; A61B 2017/2212; A61B 17/32002
See application file for complete search history.

(56) References Cited

U.S. PATENT DOCUMENTS 5,037,379 A 8/1991 Clayman et al.
5,176,687 A 1/1993 Hasson et al.
(Continued)

FOREIGN PATENT DOCUMENTS

CN 103690200 4/2014
CN 104887323 9/2015
(Continued)

OTHER PUBLICATIONS

Isakov, A New Laparoscopic Morcellator Using an Actuated Wire Mesh and Bag, Journal of Medical Devices, Mar. 31, 2014.
(Continued)

*Primary Examiner* — Katrina M Stransky
(74) *Attorney, Agent, or Firm* — Workman Nydegger

(57) ABSTRACT

A minimally-invasive tissue retrieval device includes a flexible, liquid-impermeable bag with wires attached to the interior surface by an attachment mechanism that releases the wires when pulled. The wires extend into the bag from opposing sides of the bag opening, down to the bottom of the bag. Ends of the wires extend vertically upward out of the opening and are attachable to a wire retracting element rotatably attached to a housing, such that rotation of the retracting element relative to the housing winds the wires about the retracting element, pulling them away from the interior surface, and upward towards the opening. The bag is insertable into a surgical cavity, where a tissue sample is inserted into the bag. Rotatably-retracting the wires cuts through the tissue, which can then be removed in sections through the opening positioned outside the surgical cavity to prevent the spread of tissue fragments.

20 Claims, 6 Drawing Sheets

(56) References Cited

U.S. PATENT DOCUMENTS

| | | |
|---|---|---|
| 5,215,521 A | 6/1993 | Cochran et al. |
| 5,320,627 A | 6/1994 | Borsanyi et al. |
| 5,341,815 A | 8/1994 | Cofone et al. |
| 5,465,731 A | 11/1995 | Bell et al. |
| 5,480,404 A | 1/1996 | Kammerer et al. |
| 5,562,694 A | 10/1996 | Sauer et al. |
| 5,611,803 A | 3/1997 | Heaven et al. |
| 5,647,372 A | 7/1997 | Tovey et al. |
| 5,681,324 A | 10/1997 | Kammerer et al. |
| 5,735,289 A * | 4/1998 | Pfeffer .............. A61B 17/00234 600/562 |
| 5,788,709 A | 8/1998 | Riek et al. |
| 5,895,392 A | 4/1999 | Riek et al. |
| 6,019,770 A | 2/2000 | Christoudias |
| 6,537,273 B1 | 3/2003 | Sosiak |
| 6,659,105 B2 | 12/2003 | Burbank et al. |
| 6,951,533 B2 | 10/2005 | Foley |
| 7,547,310 B2 | 6/2009 | Whitfield |
| 7,670,346 B2 | 3/2010 | Whitfield |
| 7,955,292 B2 | 6/2011 | Leroy et al. |
| 8,137,372 B2 | 3/2012 | Kondoh et al. |
| 8,628,540 B2 | 1/2014 | Freudenthal |
| 8,827,968 B2 | 9/2014 | Taylor et al. |
| 8,920,431 B2 | 12/2014 | Shibley et al. |
| 9,370,341 B2 | 6/2016 | Ceniccola et al. |
| 9,498,238 B2 | 11/2016 | Smith et al. |
| 9,549,747 B2 | 1/2017 | Carlson |
| 9,592,067 B2 | 3/2017 | Hartoumbekis |
| 9,655,644 B2 | 5/2017 | Collins |
| 9,877,893 B2 | 1/2018 | Taylor et al. |
| 9,901,329 B1 | 2/2018 | Polo |
| 2004/0097960 A1 | 5/2004 | Terachi et al. |
| 2006/0200169 A1 | 9/2006 | Sniffin |
| 2006/0200170 A1 | 9/2006 | Aranyi |
| 2007/0073251 A1 | 3/2007 | Zhou et al. |
| 2007/0135780 A1 | 6/2007 | Pagedas |
| 2008/0221604 A1 * | 9/2008 | Kondoh ........... A61B 17/32056 606/170 |
| 2009/0043315 A1 | 2/2009 | Moon |
| 2011/0299799 A1 | 12/2011 | Towe |
| 2016/0030073 A1 * | 2/2016 | Isakov ................. A61B 17/221 606/113 |
| 2016/0100857 A1 * | 4/2016 | Wachli ............... A61B 17/3439 600/204 |
| 2016/0157843 A1 * | 6/2016 | Dickson .......... A61B 17/00234 606/47 |
| 2016/0199050 A1 | 7/2016 | Radl et al. |
| 2016/0256145 A1 | 9/2016 | Ceniccola et al. |
| 2016/0296244 A1 | 10/2016 | Thomas et al. |
| 2016/0346000 A1 | 12/2016 | Abreu |
| 2017/0035452 A1 | 2/2017 | Smith et al. |
| 2017/0119455 A1 | 5/2017 | Johnson et al. |
| 2017/0150951 A1 | 6/2017 | Ling et al. |
| 2017/0325798 A1 | 11/2017 | Prior |

FOREIGN PATENT DOCUMENTS

| | | |
|---|---|---|
| CN | 105943135 | 9/2016 |
| DE | 4212430 | 10/1993 |
| EP | 0465051 | 8/1995 |
| EP | 0577063 | 5/1996 |
| EP | 0739604 | 10/1996 |
| EP | 0904003 | 3/1999 |
| EP | 1679040 | 7/2006 |
| EP | 1714616 | 10/2006 |
| EP | 1773204 | 1/2008 |
| EP | 1700569 | 11/2008 |
| EP | 1707130 | 12/2008 |
| EP | 2020207 | 2/2009 |
| EP | 1707126 | 12/2009 |
| EP | 1967146 | 4/2012 |
| EP | 2052688 | 6/2012 |
| EP | 2617365 | 7/2013 |
| EP | 2813185 | 12/2014 |
| EP | 2544596 | 8/2016 |
| EP | 3123965 | 2/2017 |
| EP | 2184014 | 12/2017 |
| JP | H08140983 | 6/1996 |
| WO | WO 2014158880 A1 * | 10/2014 ........... A61B 17/221 |
| WO | 2016135192 | 9/2016 |
| WO | 2016196399 | 12/2016 |
| WO | 2017083694 | 5/2017 |

OTHER PUBLICATIONS

Taylan, Contained Morcellation: Review of Current Methods and Future Directions, Frontiers in Surgery, Mar. 14, 2017.

* cited by examiner

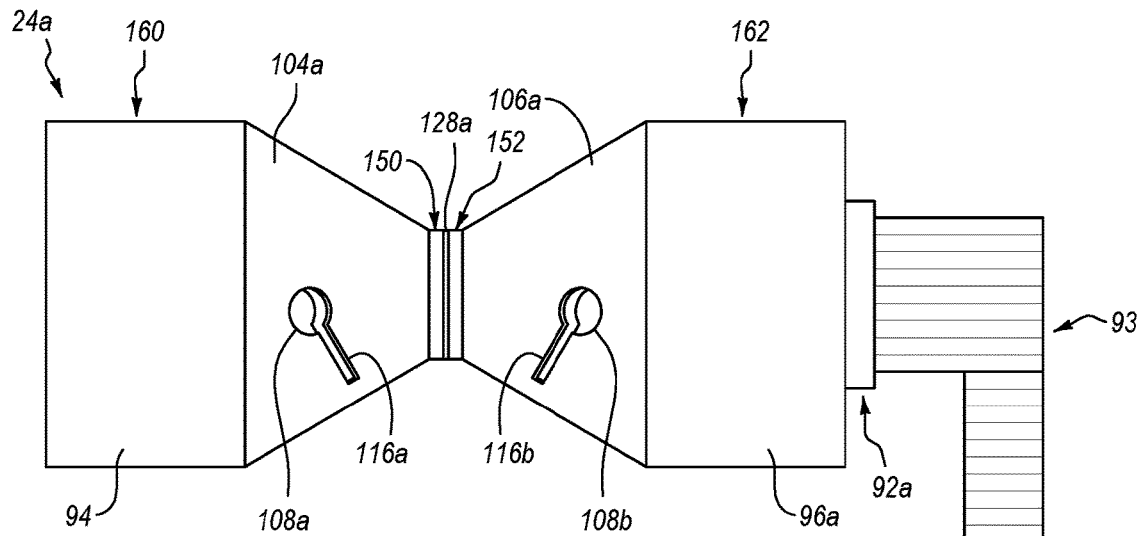
FIG. 6
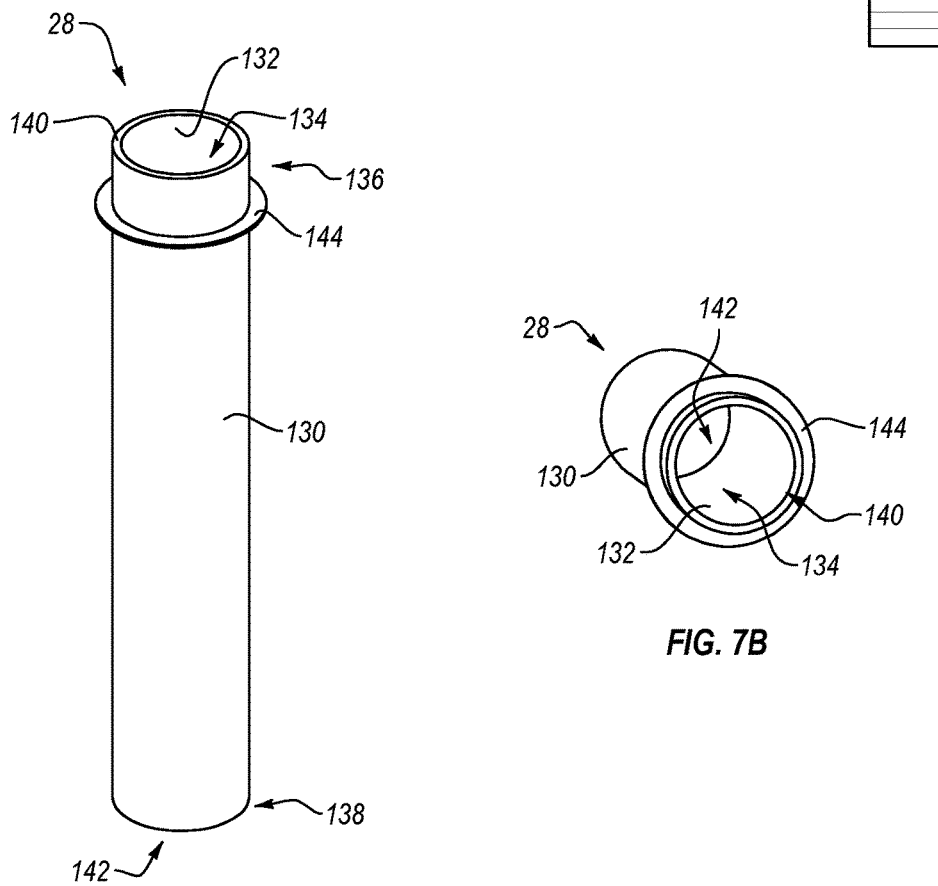
FIG. 7A
FIG. 7B

ORGANIC SPECIMEN ORIENTATION, SEGMENTATION AND RETRIEVAL DEVICE

CROSS-REFERENCE TO RELATED APPLICATIONS

The present application claim the benefit of priority to U.S. Provisional Application No. 62/144,493, filed on Apr. 8, 2015, entitled "Organic Specimen Orientation, Segmentation and Retrieval Device," the entire content of which is incorporated herein by specific reference.

BACKGROUND

1. Technical Field

The present disclosure relates generally to medical surgical devices and more particularly to minimally invasive, biological tissue retrieval devices and methods of retrieving the organic tissue from a surgical cavity by segmentation while maintaining tissue orientation.

2. Relevant Technology

The development of minimally invasive approaches to gynecologic and other surgeries has allowed physicians to remove abdominal, pelvic, and other masses with shorter hospital stays, faster recovery, fewer intra-operative complications and fewer post-operative complications. With these advances in technology and technique have come several obstacles that influence the direction of the field and patient care.

One major obstacle in the field of minimally invasive surgery relates to the topic of morcellation. By way of illustration, once a large (pelvic) mass is separated for the body it is a challenge to remove the mass through the small surgical entry incisions in a safe and reliable way. Historically, the mass may have to be removed through the vagina or through creating a larger incision to facilitate removal of the mass intact or through manual morcellation. Morcellation, as known in the art, is a term referring to cutting or dividing a mass into smaller pieces to facilitate removal through a smaller opening. Over time, the power morcellator was developed. By using a spinning or cutting tool, the mass was pulled through the power morcellator in a way that enabled the physician to reduce the size of a mass and remove elongated portions at the same time.

With the widespread adoption of both manual morcellation and power morcellation, several concerns have arisen. A first concern is safety. Although undiagnosed cancer is a rare occurrence, with the use of morcellation (manual or power) there is always a risk of potentially spreading or seeding an undiagnosed cancer. This has led to lawsuits, lifelong implications on cancer survival for individuals affected, and a countrywide hesitation to morcellate pelvic masses. A second concern is operation and recovery time. Both manual and power morcellation have significant implications on operative time.

A third concern involves cancer staging. Morcellation often distorts tissue, and in the process will disrupt the orientation of cells within the mass. Orientation of cells is important for evaluation of cancerous tissue. By keeping tissue naturally-oriented, the histology (or anatomy) of cells is maintained or preserved, such that a pathologist can look at the cell under a microscope to see if the cancerous cells have reached to the margins or border of the tissue (e.g., to help determine the stage of the cancer). Cancer stage often determines cancer treatment. Morcellation does not allow tissue to be evaluated in this way, and therefore the opportunity to appropriately stage the cancer can be lost.

Accordingly, there are a number of obstacles, disadvantages, and challenges in conventional surgical procedure and apparatus that can be addressed.

BRIEF SUMMARY

Implementations of the present invention overcome or solve one or more of the foregoing or other problems in the art with minimally invasive, biological tissue retrieval devices and methods of retrieving the organic tissue from a surgical cavity by segmentation while maintaining tissue orientation. At least one implementation includes a tissue removal device comprising a bag assembly that includes a bag having an interior surface and at least one wire attached to the bag and extending along the interior surface. The bag can have a flexible and/or liquid-impermeable configuration and/or can be formed of at least one malleable film or sheet material. In some implementations, one or more ends of the wire(s) can be detached from the interior surface and/or extend out through the opening of the bag.

The bag or bag assembly can also include a wire attachment mechanism that maintains the wire(s) oriented along the interior surface in the absence of a detaching force, and releases the wire(s) when a detaching force is applied or when a detaching event occurs. The wire attachment mechanism can include an adhesive and/or overlay that reversibly and/or releasably secures the wires to the interior surface. The bag can be collapsed and inserted into a surgical cavity through a surgical opening, and optionally secured to a keeping device disposed at the surgical opening. A tissue sample to be retrieved can be surgically detached from the patient body and inserted into the bag, within the surgical cavity, through the bag opening.

Certain implementations include a wire detaching member, comprising a wire retracting element rotatably attached to a housing. The housing can include a lower access opening (through which the wire(s) of the bag assembly can pass into a receiving area of the housing) and/or an upper operating opening (through which a user can operate aspects of the apparatus). The wire(s) of the bag assembly can be connectable to the wire detaching member, or retracting element thereof, such that rotation of the wire retracting element relative to the housing can wrap or wind the wire(s) about the wire retracting element. The wire retracting element can have a substantially V-shaped, hourglass-shaped, and/or dumbbell shaped (at least partially recessed) configuration and/or resemble the shape thereof, or have another at least partially recessed configuration, such that the wrapped wires are collected to a central or middle portion of the wire retracting element.

The wire(s) can extend vertically upward out of the bag, and can be connected to the wire retracting element through an attachment mechanism. Accordingly, the wire detaching member can be disposed vertically above the bag assembly such that rotation of the wire retracting element provides an upward force that pulls the wire(s) vertically upward out of the bag (e.g., toward the housing). Rotation of the wire retracting element can wrap or wind the wire(s) around the wire retracting element, thereby shortening or tightening the wires around the tissue sample as the wires are drawn up.

Continued rotation of the wire retracting element can provide sufficient force to pull the wires through the tissue sample, thereby sectioning the tissue sample into two or more tissue sections. The device can optionally include a handle with which to stabilize the wire detaching member during operation and/or a ratcheting mechanism with which to rotate the wire retracting element within the housing. The housing can also include one or more wire retaining elements, such as recessed notches, to reversibly secure the wire(s) to the housing (e.g., prior to attachment to the wire retracting element).

In some implementations, a tubular positioning member can extend from the housing, or lower access opening thereof, and into the bag. Ends of the wire(s) can be fed through the positioning member and into the receiving area of the housing, to be connected to the wire retracting element. During rotation of the wire retracting element, the positioning member can restrict upward movement of the tissue sample by providing back-pressure on the tissue sample. The positioning member can also help to maintain a constant orientation of the tissue sample during sectioning by directing the path of the wires from the bag to the wire retracting element.

Additional features and advantages of exemplary implementations of the present invention will be set forth in the description which follows, and in part will be obvious from the description, or may be learned by the practice of such exemplary implementations. The features and advantages of such implementations may be realized and obtained by means of the instruments and combinations particularly pointed out in the appended claims. These and other features will become more fully apparent from the following description and appended claims, or may be learned by the practice of such exemplary implementations as set forth hereinafter.

BRIEF DESCRIPTION OF THE DRAWINGS

In order to describe the manner in which the above-recited and other advantages and features of the present disclosure can be obtained, a more particular description of various implementations of the present disclosure will now be rendered with reference to the appended drawings, in which the exemplary implementations are illustrated. It is appreciated that these drawings depict only typical implementations of the present disclosure and are not, therefore, to be considered limiting of its scope.

FIG. 6 illustrate perspective views of a retracting element in accordance with another implementation of the present disclosure;

FIGS. 7A-7B illustrate perspective views of a positioning member in accordance with an implementation of the present disclosure.

DETAILED DESCRIPTION

Figure 1:
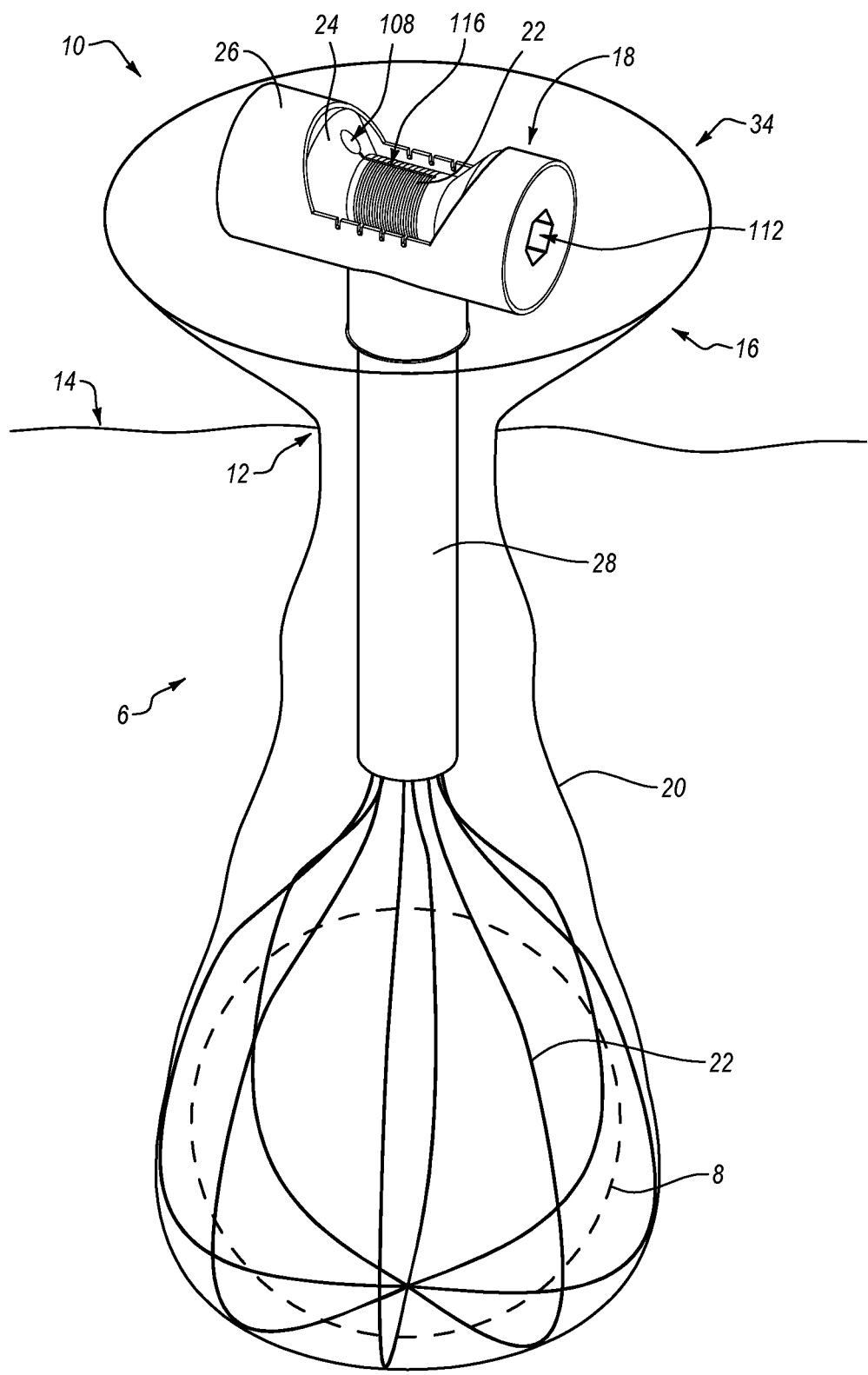
FIG. 1 illustrates a perspective view of a tissue retrieval device in accordance with an implementation of the present disclosure.

Before describing the present disclosure in further detail, it is to be understood that this disclosure is not limited to the description of the particularly exemplified systems, methods, and/or products that may vary from one implementation to the next. Thus, while certain implementations of the present disclosure will be described in detail, with reference to specific configurations, parameters, features (e.g., components, members, elements, parts, and/or portions), etc., the descriptions are illustrative and are not to be construed as limiting the scope of the claimed invention. In addition, the terminology used herein is for the purpose of describing the implementations, and is not necessarily intended to limit the scope of the claimed invention.

Unless defined otherwise, all technical and scientific terms used herein have the same meaning as commonly understood by one of ordinary skill in the art to which the present disclosure pertains.

Various aspects of the present disclosure, including systems, processes, and/or products may be illustrated with reference to one or more implementations or embodiments, which are exemplary in nature. As used herein, the terms "embodiment" and "implementation" mean serving as an example, instance, or illustration, and should not necessarily be construed as preferred or advantageous over other aspects disclosed herein. In addition, reference to an "implementation" of the present disclosure or invention includes a specific reference to one or more embodiments thereof, and vice versa, and is intended to provide illustrative examples without limiting the scope of the invention, which is indicated by the appended claims rather than by the following description.

As used herein, the term "systems" also contemplates devices, apparatus, compositions, assemblies, kits, and so forth. Similarly, the term "method" also contemplates processes, procedures, steps, and so forth. Moreover, the term "products" also contemplates devices, apparatus, compositions, assemblies, kits, and so forth.

As used throughout this application the words "can" and "may" are used in a permissive sense (i.e., meaning having the potential to), rather than the mandatory sense (i.e., meaning must). Additionally, the terms "including," "having," "involving," "containing," "characterized by," as well as variants thereof (e.g., "includes," "has," and "involves," "contains," etc.), and similar terms as used herein, including the claims, shall be inclusive and/or open-ended, shall have the same meaning as the word "comprising" and variants thereof (e.g., "comprise" and "comprises"), and do not exclude additional, un-recited elements or method steps, illustratively.

It will be noted that, as used in this specification and the appended claims, the singular forms "a," "an" and "the" include plural referents unless the context clearly dictates otherwise. Thus, for example, reference to a "wire" includes one, two, or more wires. Similarly, reference to a plurality of referents should be interpreted as comprising a single referent and/or a plurality of referents unless the content and/or context clearly dictate otherwise. Thus, reference to "wires" does not necessarily require a plurality of such wires. Instead, it will be appreciated that independent of conjugation; one or more wires are contemplated herein.

As used herein, directional, positional, and/or orientational terms, such as "top," "bottom," "left," "right," "up," "down," "upper," "lower," "inner," "outer," "internal," "external," "interior," "exterior," "proximal," "distal" and so forth can be used arbitrarily and/or solely to indicate relative directions, positions, and/or orientations and may not be otherwise intended to limit the scope of the disclosure, including the specification, drawings, and/or claims.

Various aspects of the present disclosure can be illustrated by describing components that are bound, coupled, attached, connected, and/or joined together. As used herein, the terms "bound," "coupled", "attached", "connected," and/or "joined" are used to indicate either a direct association between two components or, where appropriate, an indirect association with one another through intervening or intermediate components. In contrast, when a component is referred to as being "directly bound," "directly coupled", "directly attached", "directly connected," and/or "directly joined" to another component, no intervening elements are present or contemplated.

To facilitate understanding, like references (i.e., like naming of components and/or elements) have been used, where possible, to designate like elements common to the figures. Specifically, in the exemplary implementations illustrated in the figures, like structures, or structures with like functions, will be provided with similar reference designations, where possible. Specific language will be used herein to describe the exemplary implementations. Nevertheless it will be understood that no limitation of the scope of the disclosure is thereby intended. Rather, it is to be understood that the language used to describe the exemplary implementations is illustrative only and is not to be construed as limiting the scope of the disclosure (unless such language is expressly described herein as essential).

It will also be appreciated that where multiple possibilities of values or a range of values (e.g., less than, greater than, at least, and/or up to a certain value, and/or between two recited values) is disclosed or recited, any specific value or range of values falling within the disclosed range of values is likewise disclosed and contemplated herein. Thus, disclosure of an illustrative measurement or amount less than or equal to about 10 units or between 0 and 10 units includes, illustratively, a specific disclosure of: (i) a measurement or amount of 9 units, 5 units, 1 units, or any other value between 0 and 10 units, including 0 units and/or 10 units; and/or (ii) a measurement or amount between 9 units and 1 units, between 8 units and 2 units, between 6 units and 4 units, and/or any other range of values between 0 and 10 units.

The headings used herein are for organizational purposes only and are not meant to be used to limit the scope of the description or the claims.

Solutions to the obstacles of tissue removal need to be both safe and fast and may benefit by maintain the orientation of the mass for staging purposes. Several alternatives to traditional use of power morcellation in the open abdomen have been developed, but these have increasing levels of complexity and technical difficulty. Implementations of the present disclosure are directed towards medical surgical devices and more particularly to minimally invasive, biological tissue retrieval devices and methods of retrieving the organic tissue from a surgical cavity by segmentation. The devices and methods provide easy-to-use and cost-effective solutions to the obstacles of tissue removal, are safe and fast in operation, and/or maintain tissue orientation for histological analysis.

One aspect of the present disclosure relates to a tissue removal device that may be used during minimally invasive surgery to remove large tissue masses through a small incision, such as, for example, a 10-15 mm laparoscopic port site or a vaginal incision. The tissue removal device may include a (liquid-impermeable) bag that may contain the tissue prior to and during segmentation and may therefore prevent the spread of tissue throughout the abdomen during segmentation. Current methods of removing large tissue masses during laparoscopic surgery include using morcellation, which has been found to spread cancerous tissue throughout the abdomen during the debulking and removal of the tissue. Rather than using blades powered electrically as used by a morcellator, the present disclosure relates to a tissue removal device that may utilize wires that are integrated into an impermeable bag and a mechanical system to segment and debulk the tissue to be removed.

During a laparoscopic hysterectomy, for example, small, approximately 1 cm incisions are made to facilitate the placement of laparoscopic instruments and a two-dimensional camera. With the use of coagulation, cutting, and tissue manipulation the uterus is separated for the body, leaving a surgical opening at the distal end of the vagina, where the uterus was attached. If the size of the uterus allows, it can be removed through the vaginal surgical opening prior to suturing the vaginal tissue to close the opening, thereby avoiding large, (open) abdominal surgical opening. Larger uteruses may need to be divided into smaller parts in order to fit through the surgical opening. Segmentation allows uteruses of virtually any size to be sectioned and removed through the surgical opening. Other surgical procedures, such as splenectomies, can apply segmentation to remove tissue through small (abdominal) surgical openings, as well.

Implementation of the present disclosure, which relates to removing large tissue specimens during laparoscopic or other minimally invasive surgery, assists in the safe and fast removal of a large uterus or other tissue sample. By way of example, the bag is inserted through a surgical opening into the surgical cavity, where the tissue or mass is placed in the impermeable bag laparoscopically. The open end of the bag is then removed through the vaginal opening (or laparoscopic port).

A series of wires that line the interior of the impermeable bag are detached from the opening of the bag and passed through a tubular positioning member, which comprises a long (semi-rigid) tube that directs force through the wires directly on the mass being removed. The ends of the wires are introduced to a rotatable wire retracting element that is able to produce a (pulling) force on the wires as the wire retracting element is rotated within its housing. As the wires are tightened, the wires advance (e.g., cut, slice, etc.) through the tissue, sectioning the tissue contained in the bag into elongated pieces. The positioning member retains the tissue in the bag, inhibiting the tissue from being pulled out of the opening of the bag as the wires are wound up by the wire retracting element.

Illustratively, pulling a series of four (4) wires through the tissue can section the tissue into eight (8) pieces. Each of the cut pieces can then be removed through the vaginal opening or laparoscopic port. Because the wires are pulled through the tissue in a substantially constant (upward) direction while the positioning member inhibits movement of the tissue (e.g., in the (upward) direction and/or rotationally within the surgical cavity), the (elongated) pieces of tissue can retain a more natural orientation of the cells relative to one another, such that the cellular structure of the tissue may be analyzed by a pathologist in order to determine the histology and stage of any cancer, if any, that are present in the tissue. This approach also protects against undiagnosed cancer spreading within the surgical cavity (as the tissue is only removed from the bag outside of the patient body) and provides a fast alternative to power and manual morcellation.

As used herein, "minimally invasive surgery," includes endoscopic, laparoscopic, thoracoscopic, arthroscopic, urethroscopic, bronchoscopic, so called "keyhole" surgery, or any other procedure designed to reach internal tissue (e.g., an organ, tumor, mass, etc.) through very small incisions or natural orifice (e.g., mouth, nostril, vagina, rectum, etc.). Such procedures usually utilize an endoscope. Illustratively, a thin, flexible tube with a video camera is inserted through the small incision or orifice. The tube has a channel to utilize tiny surgical instruments, which the surgeon uses while viewing the organs on a computer monitor. The technique allows the surgeon to see inside the patient's body and operate through a much smaller incision than would otherwise be required of traditional open surgery, which involves a large incision and viewing the surgical site with the naked eye or direct magnification.

Benefits of minimally invasive surgical procedures can include smaller incisions, fewer incisions, or no incision at all. In addition, reduced pain, recovery time, blood loss, hospital stay time, and risk of infection are also associated with minimally invasive surgery. Minimally invasive surgery has been used to treat, repair, and remove tissue from the surgical cavity. Illustrative examples of minimally invasive, tissue removal (or retrieval) surgery include hysterectomy, appendectomy, splenectomy, cholecystectomy (gallbladder), nephrectomy (kidney), and removal of tumors (benign and malignant), lesions, cysts, etc.).

As used herein, "impermeable" refers to the property of restricting passage thereby. For instance, a liquid-impermeable bag restricts the flow or diffusion of liquids through the bag material. It will be appreciated that while the term "impermeable" implies impassibility on a physical, material level, impermeable substances may still be penetrable on a microscopic or molecular level without necessarily departing from the scope of this disclosure.

Reference will now be made to illustrative implementations of the present disclosure depicted in or otherwise illustrated by the appended figures. Illustrated in FIG. 1 is an exemplary implementation of a tissue retrieval device 10 incorporating features of the present disclosure. As depicted in FIG. 1, tissue retrieval device 10 can be disposed within and/or extend through a surgical opening 12 in a patient body 14. Opening 12 can comprise an external, (laparoscopic) or an internal (e.g., vaginal-cervical) opening or incision.

Device 10 can include a bag assembly 16, comprising a flexible bag 20 and one or more wires 22 disposed in bag 20. Device 10 can also include a retraction assembly 18, in some implementations. Retraction assembly 18 can include a wire retracting element 24, a housing 26, and an optional positioning member 28 extending from housing 26. Retracting element 24 can be rotatably attached to and/or within housing 26. Wire(s) 22 can extend from bag 20, through optional positioning member 28, and into housing 26, where wire(s) 22 can be connect to retracting element 24.

Various features and components of device 10, and other illustrative apparatus and methods, will now be discussed in further detail below.

Bag Assemblies

Figure 2A:
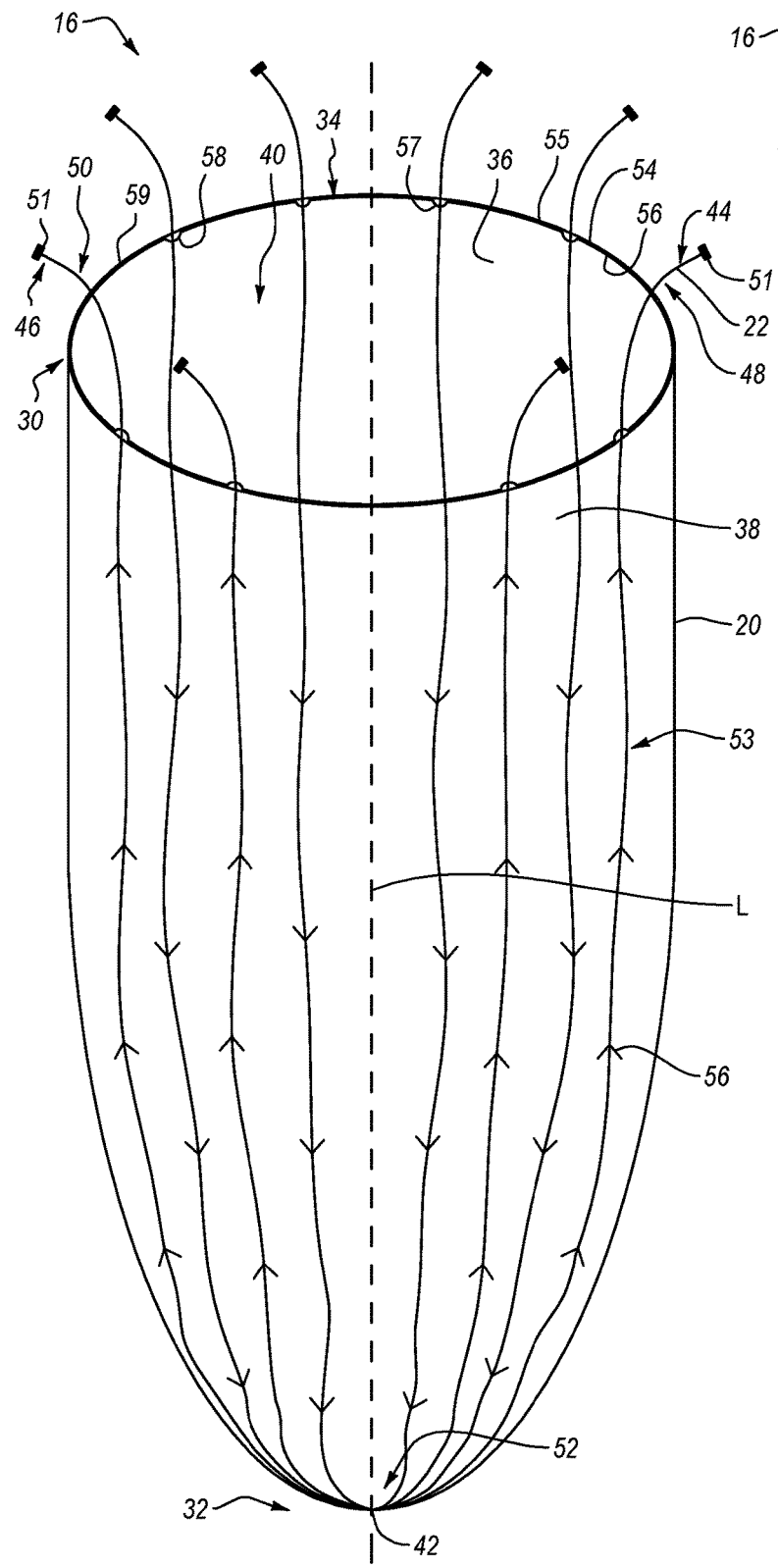
FIG. 2A illustrates a perspective view of a bag assembly in an expanded configuration in accordance with an implementation of the present disclosure.

Depicted in FIG. 2A is one implementation of an illustrative bag assembly 16 comprising flexible bag 20 and a plurality of wires 22 disposed in bag 20. Bag 20 can have an opening 34 disposed at a first end 30 thereof, and a closed bottom 42 disposed at an opposing second end 32 thereof. Bag 20 can comprise an internal surface 36 and an external surface 38, each extending from first and 30 to second end 32. Internal surface 36 of bag 20 can bound in the internal compartment 40. Opening 34 can be in communication with internal compartment 40.

In at least one implementation, bag 20 can be formed or comprised of one or more sheets or layers of flexible, film material. The material of bag 20 can also be durable and/or resistant to tearing, breaking, and/or puncture, while being malleable, collapsible, and/or resiliently deformable without cracking, breaking, and/or tearing. The flexible material of bag 20 can also be liquid-impermeable. For instance, bag 20 can be formed of (thin-gauge) polyurethane and/or other plastic or polymeric material(s). In certain implementations, flexible bag 20 can be substantially impermeable to solids, liquids, and/or gases.

Bag 20 can have a variety of shapes and/or sizes (e.g., in order to facilitate the removal of various sizes of tissue). As depicted in FIG. 2A, for instance, bag 20 can have a substantially tubular, elongated configuration with the distance between opening 34 and closed bottom 42 being approximately twice as large as the diameter of opening 34. It will be appreciated, however, that the present disclosure is not so limited. Rather, bag 20, opening 34, and/or closed bottom 42, can have any suitable size and/or dimension(s). In certain implementations, bag 20 can define a longitudinal direction (L) extending through compartment 40, from a center of closed bottom 42 to a center of opening 34. Bag 20 can have a substantially constant size (e.g., diameter) extending from a portion of first end 30 to a portion of second end 32. Bag 20 can, alternatively, be at least partially tapered (e.g., from or between opening 34 and closed bottom 42) in some implementations.

Wires 22 can be attached to bag 20 or internal surface 36 thereof. For instance, each of wires 22 can extend along interior surface 36 from a first portion of opening 34 to a second portion of opening 24 opposite the first portion by extending along closed bottom 42. Accordingly, a first end 44 of a first wire 22, and a second, opposing end 46 of the first wire 22, can each be disposed adjacent to first end 30 of bag 20 (e.g., on opposing sides of opening 34), with a middle portion (or length) 53 of wire 22 extending along interior surface 36, from first end 30 of bag 20, (down) to closed bottom 42, and back (up) to first end 30 (e.g., in a U-shaped configuration). A second wire 22 can extend from an adjacent third portion of opening 34 (e.g., between the first portion of the second portion), along interior surface 36 to closed bottom 42, overlaying a portion of middle 53 of first wire 22, and backup along interior surface 36 to a fourth portion of opening 34 opposite the third portion. Accordingly, in at least one implementation, each wire 22 can extend symmetrically along interior surface 36, with successive wires 22 overlaying previously laid wires 22 at one or more crossover points 52 (e.g., disposed at second end 32 and/or closed bottom 42).

As further depicted in FIG. 2A, wire 22 can also comprise a first extension 48 protruding from the first portion of opening 34 and an optional second extension 50 protruding from the second portion of opening 34. First extension 48, and optionally second extension 50, can protrude from the first portion of opening 34 in longitudinal direction (L). It will be appreciated, however, that the present disclosure is not so limited. For instance, in an alternative implementation, one or more wires 22 and/or extension thereof may not extend beyond opening 34. Alternatively, one or more ends 44, 46 of one or more wires 22 can be disposed at or adjacent to opening 34. As illustrated in the depicted implementation, each wire 22 extends beyond opening 34 in a substantially similar manner and/or a substantially similar distance or length. It will be appreciated, however, that different ends 44, 46 of one or more wires 22 can extend different distances or lengths beyond opening 34 in one or more implementations.

First end 44, and optionally, the second end 46, of wire 22 can also have a securing element 51 disposed thereat. In the depicted implementation, securing element 51 comprises an end piece, such as a wire or cable nipple, (e.g., barrel nipple, pear nipple, etc.), beads, or other end piece configured for securing wire 22 (e.g., in a slot-and-insert or lock-and-key fashion). In an alternative implementation, securing element 51 can comprise a ring, loop, or other attachment member configured for securing wire 22 (e.g., in a hook-and-loop fashion). In certain implementations, securing elements 51 can also comprise a magnetic property. Accordingly, securing elements 51 can be formed of at least one metal or metal alloy, magnet, or other suitable material.

In at least one implementation, wire 22 and/or securing elements 51 thereof can include one or more sequential indicators, such as numbers, letters, colors, shapes, etc. In certain implementations, opposing securing elements 51 and/or ends 44, 46 of wires 22 can have, include, and/or comprise the same or substantially same sequential indicator (e.g., So as to indicate opposing ends of the same wire 22). As described in further detail below, such sequential indicators can provide an indication as to the overlay order of wires 22. For instance, a final overlaid wire 22 can have a first sequential indicator disposed thereon (e.g., on securing elements 51). Similarly, a second-to-final overlaid wire 22 can have a second sequential indicator disposed thereon, and so forth. Likewise, a first laid wire 22 can have a final sequential indicator disposed thereon.

Bag assembly 16 can also include a wire attachment mechanism (or fastener) adapted and/or configured to (detachably) secure wires 22 within compartment 40 or along interior surface 36 of bag 20. The wire attachment mechanism 56 can be disposed within inner compartment 40 of bag 20. In some implementations, the wire attachment mechanism (or fastener) can comprise a covering or overlay connected to interior surface 36 and extending over the portion of wires 22 disposed within compartment 40, an adhesive that detachably attaches wires 22 to internal surface 36 of bag 20, or both.

In the depicted implementation a wire attachment mechanism (or fastener) 56 comprises a sheet or film covering or layer. The sheet or film covering or layer can be connected to interior surface 36 at one or more attached portions 59 (adjacent to wires 22), with one or more looped regions 58 extending over wires 22. Attached portion(s) 59 can be connected to interior surface 36 by means of an adhesive, welding, stitching, or other fastener or attachment mechanism. In at least some implementations, looped regions 58 can be substantially unsecured from interior surface 36. Alternatively, looped regions 58 can also be attached (e.g., over wires 22) by means of an adhesive or other fastener or attachment mechanism. In certain implementations, wire attachment mechanism (or fastener) 56 can comprise a supplemental bag layer disposed across or about (substantially all of or the entire) interior surface 36.

In some implementations, wire attachment mechanism (or fastener) 56 can comprise a plurality of coverings or overlays. For instance, wire attachment mechanism (or fastener) 56 can comprise plurality of elongated coverings or overlays attached to internal surface 36 on opposing sides of wires 22. The elongated coverings or overlays can extend from first end 30, or a portion of bag 20 adjacent thereto, to second end 32, or a portion of bag 20 adjacent thereto.

In at least one implementation, wire attachment mechanism 56 can comprise one or more (e.g., a plurality of) fasteners, such as rings, loops, anchors, staples, sutures, and/or film strips (e.g., instead of a sheet, film, or surface covering). Such fasteners can be connected to interior surface 36 (e.g., by means of an adhesive) at one or more attachment portions 59 (adjacent to wires 22). Alternatively, the fasteners can be sewn or stitched into bag 20. One or more looped regions 58 can also extend over wires 22. Looped regions 58 can retain wires 22 and can fail and/or fail to maintain wires as described above. Any suitable number of such fasteners can be connected to interior surface 36 at any number of positions along the length of wires 22, or middle portion 53 thereof.

In some implementations, wire attachment mechanism 56 can be adapted and/or configured to releasably secure wires 22 and/or maintain the position and/or orientation of wires 22 within compartment 40 or along the interior surface 36 of bag 20 in the absence of a detaching force (e.g., applied to wires 22, such as in direction (L)). Accordingly, wire attachment mechanism 56 can releasably retain wires 22 in a predetermined (starting) position and/or orientation compartment 40 or along the interior surface 36 of bag 20.

In at least one implementation, wire attachment mechanism 56 can be adapted and/or configured to fail and/or fail to maintain the position and/or orientation of wires 22 within compartment 40 or along the internal surface 36 of bag 20 in response to a detaching force or event (e.g., when a detaching force is applied (e.g., to wires 22, such as in direction (L)), or when contacted by a fluid or solvent). Such failure, or failure to maintain, can comprise a breakage, release, or dissolving of at least a portion of attachment mechanism 56. Thus, wire attachment mechanism 56 can be adapted and/or configured to release wires 22 from (being secured at or against) internal surface 36 when a detaching force is applied to wires 22 or when contacted by a fluid or solvent. For instance, in certain implementations, at least a portion of attachment mechanism 56 can comprise or be formed of a material that is dissolvable with water or other (fluid), such that the durability of at least a portion of attachment mechanism 56 is reduced (e.g., allowing wires 22 to tear through or pull away from the weakened material).

In other implementations, at least a portion of attachment mechanism 56 can be formed of a material that breaks or releases wires 22 when a sufficient force is applied thereto.

Wires 22 can be formed and/or comprised of any suitable material, including one or more metals, metal alloys, polymers, plastics, natural or synthetic fibers, etc. In some implementations, wires 22 can have diameter between about 0.05 mm and about 5 mm, preferably between about 0.1 mm and about 2 mm, more preferably between about 0.2 mm and about 1 mm, or any value or range of values therebetween. Wires 22 can also have any suitable measurement of (tensile or breaking) strength. For instance, wires 22 can have a (tensile or breaking) strength sufficient to resist breakage when pulled with about 50, 100, 150, 200, 250, 300, 350, 400, 450, 500, 550, 600, 650, 700, 750, 800, 850, 900, 950, 1000, 1100, 1200, 1300, 1400, or 1500 pounds or force, or more. Wires 22 can have a woven, braided, or other configuration adapted to increase or enhance the (tensile or breaking) strength thereof. It will also be appreciated that wires 22 can be flexible, bendable, pliable, and/or malleable. In at least one implementation, for instance, wires 22 can be flexible without retaining a crease or substantial degree of deformation.

Figure 2B:
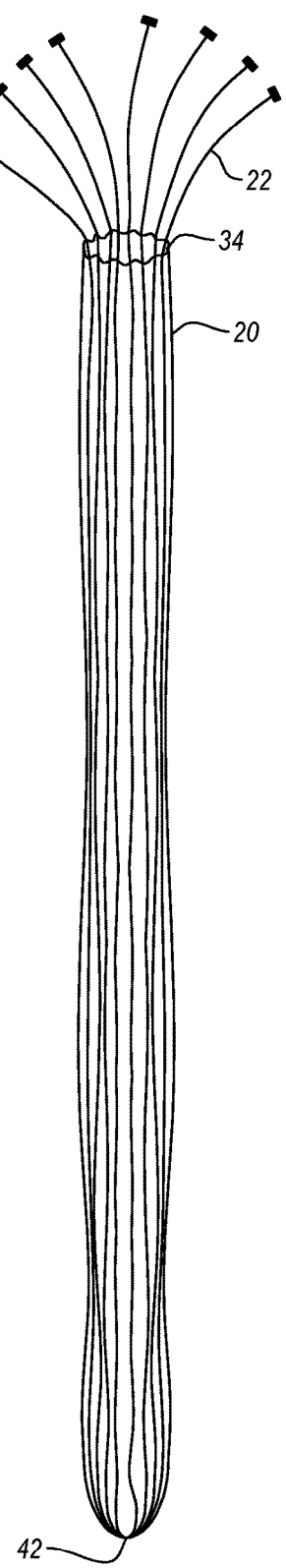
FIG. 2B illustrates a bag assembly of FIG. 2A in a collapsed configuration.

In some implementations, the wires may be integrated into bag 20 such that bag 20 can be easily inserted through surgical opening 12 and into surgical cavity 6 of patient body 14 (see FIG. 1). For instance, as depicted in FIG. 2B, bag assembly 16 can be compressed into a collapsed state, wherein the volume of compartment 40 is minimized and/or reduced. In the collapsed state, respective middle portions 53 of wires 22 can be brought into close proximity with bag 20 compressed and/or constricted around wires 22. It will also be appreciated, that in the collapsed state, bag assembly 16 can be inserted through surgical opening 12 and into surgical cavity 6 of patient body 14 (see FIG. 1) without substantially compromising the orientation of the wires within the bag and/or relative to one another. Bag assembly 16 can also be re-expanded, as depicted in FIG. 2A (e.g., within surgical cavity 6). In at least one implementation, wires 22 may not retain a substantial crease, kink, bend, or other deformation when expanded from the collapsed state, as depicted in FIG. 2B, to the expanded state, as depicted in FIG. 2A.

In certain implementations, wires 22 can have a substantially resilient and/or biasing property or configuration. For instance, in at least one implementation, wires 22 can at least partially bias bag 20 into the expanded configuration. Accordingly, after collapsing bag assembly 16 into the collapsed state, bag assembly 16 can automatically, at least partially expand back into the expanded state. In other implementations, however, bag assembly 16 can be unbiased.

In some implementations, a forming element 54 can be integrated into opening 34 of bag 20. Forming element 54 can comprise a flexible (round) ring, giving form to opening 34. Forming element 54 can be collapsible, allowing opening 34 to be disposed in the collapsed state (e.g., during insertion). Forming element 54 can also facilitate the attachment of wires 22 to the edge of bag 20. For instance, attached portions 59 of wire attachment mechanism 56 can be attached to forming element 54 in certain implementations.

Bag assembly 16 can also comprise a wire collection mechanism (e.g., lasso) 55, such as a ring or loop attached to and/or to connect all of the wires 22. For instance, wire lasso 55 can be connected to bag 20 at or adjacent to opening 34 and/or forming element 54 and can comprise a series of eyelets 57 looped around a portion of each wire 22. Eyelets 57 can be smaller than securing elements 51, such that ends 44, 46 of wires 22 can be pulled together by pulling wire lasso 55, without securing elements 51 slipping through eyelets 57. In one or more implementations, forming element 54 can comprise wire lasso 55. Alternatively, as indicated above, securing elements 51 can comprise magnets and/or metal material such that securing elements 51 and/or wires 22 can be magnetically collected.

Retraction Assemblies

Figure 3:
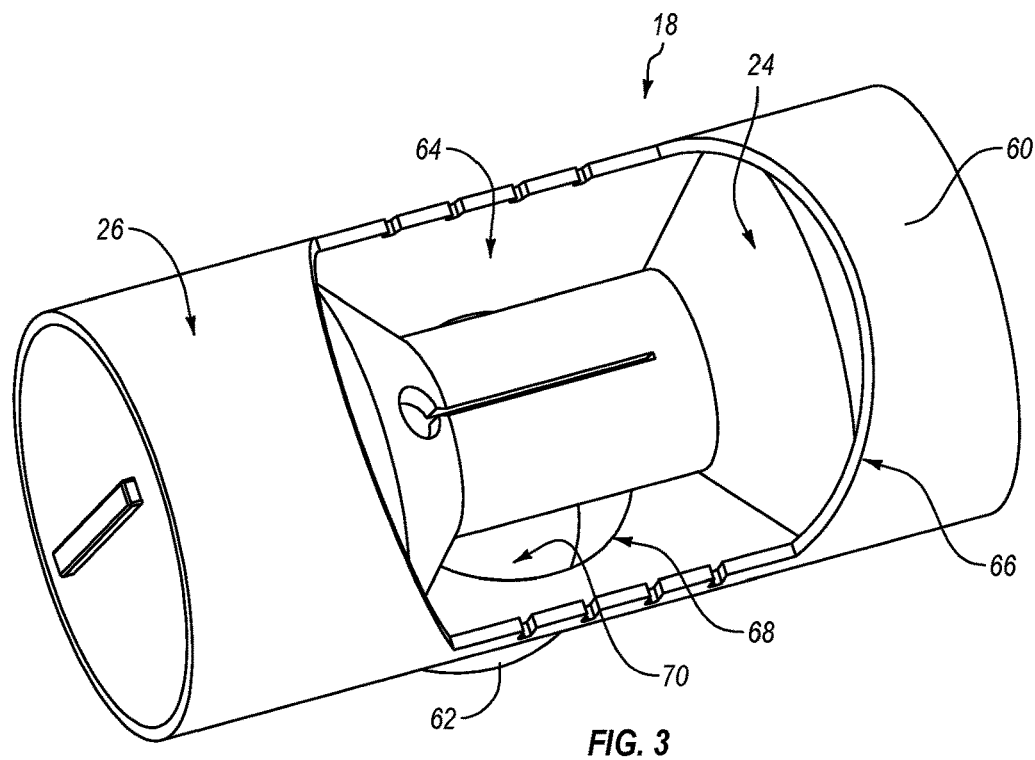
FIG. 3 illustrates a perspective view of a retraction assembly in accordance with an implementation of the present disclosure.
Figure 4:
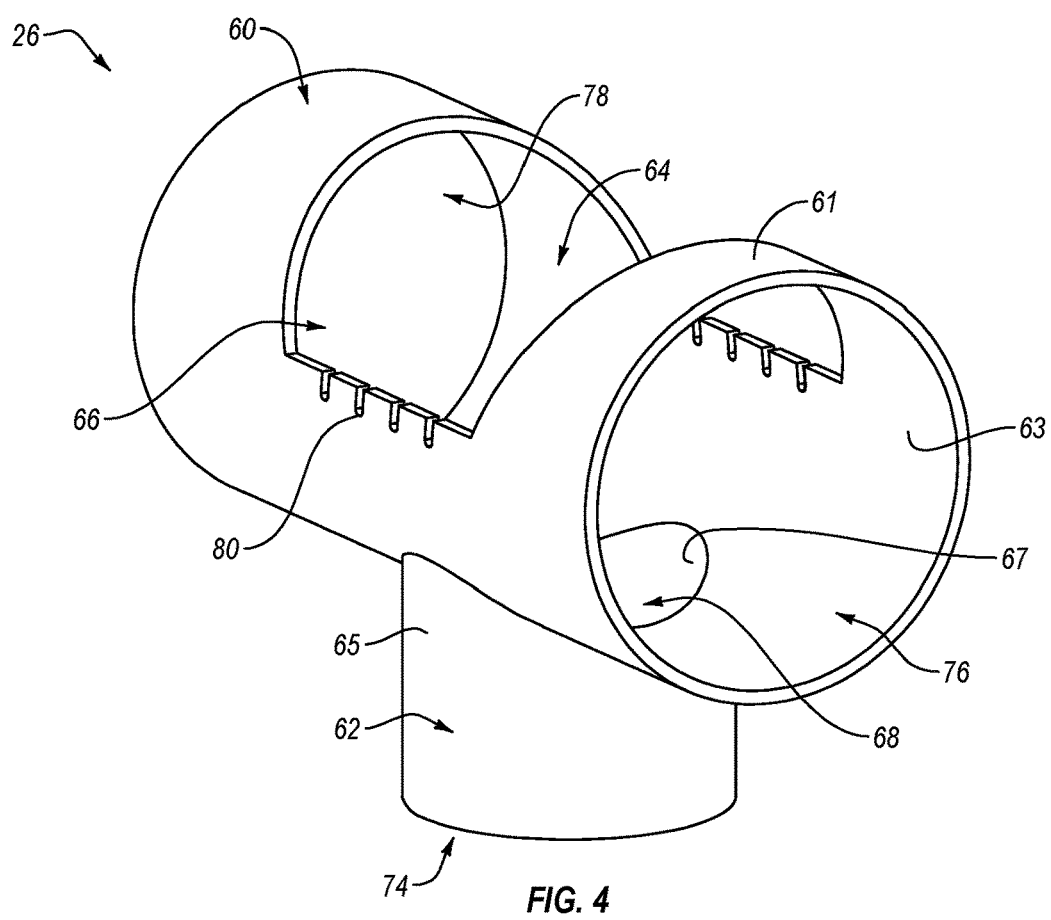
FIG. 4 illustrates a perspective view of a housing in accordance with an implementation of the present disclosure.

FIG. 3 depicts a top perspective view of retraction assembly 18. In the depicted implementation, wire retracting element 24 is rotatably disposed within a receiving area 64 of housing 26. FIG. 4 further illustrates housing 26. As illustrated in FIGS. 3 and 4, housing 26 can have a T-shaped configuration, with a tubular barrel member 60 and a tubular stem 62 extending (e.g., orthogonally) from barrel member 60. Housing 26, or tubular barrel member 60 thereof, can comprise an outer surface 61 and an inner surface 63. Similarly, tubular stem 62 can comprises an outer surface 65 and an inner surface 67.

In some implementations, tubular stem 62 can be substantially cylindrical, such that outer surface 65 and/or inner surface 67 have a rounded, circular shape or configuration. It will be appreciated, however, that stem 62 can also or alternatively be non-cylindrical (e.g., and still be tubular in nature). For instance, tubular stem 62, outer surface 65, and/or inner surface 67 can have or comprise an oval, rectangular, triangular, pentagonal, hexagonal, heptagonal, octagonal, or other shape or configuration. Tubular stem 62 can also comprise an access channel 70 extending therethrough. Inner surface 67 of tubular stem 62 can at least partially bound access channel 70. An access opening 68 disposed at the junction between barrel member 60 and tubular stem 62 provides communication between receiving area 64 of barrel member 60 and access channel 70 of tubular stem 62. Stem 62 can also have a lower distal opening 74 opposite access opening 68.

Barrel member 60 can comprise opposing open ends 76 and 78, with receiving area 64 extending at least partially therebetween. In some implementations, barrel member 60 can be substantially cylindrical, such that outer surface 61 and/or inner surface 63 have a rounded, circular shape or configuration. It will be appreciated, however, that barrel member 60 can also or alternatively be non-cylindrical (e.g., and still be tubular in nature). For instance, barrel member 60, outer surface 61, and/or inner surface 63 can have or can comprise an oval, rectangular, triangular, pentagonal, hexagonal, heptagonal, octagonal, or other shape or configuration.

Figure 8A:
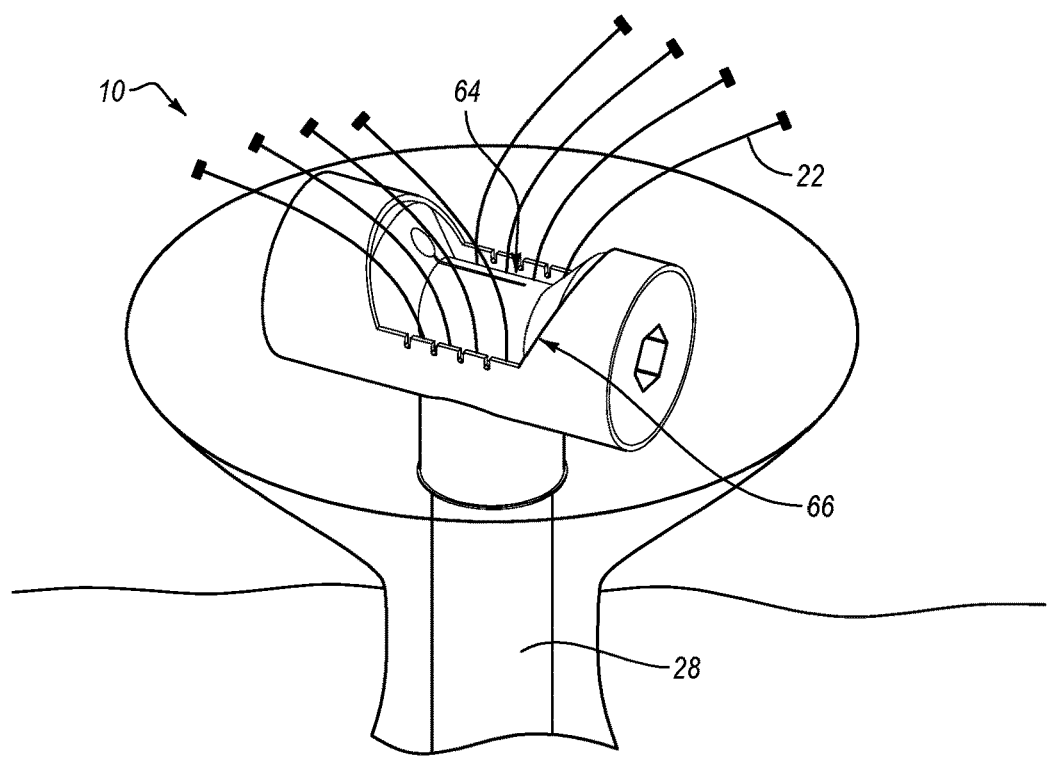
FIGS. 8A-8B illustrate perspective views of assembly configurations of the tissue retrieval device of FIG. 1.
Figure 8B:
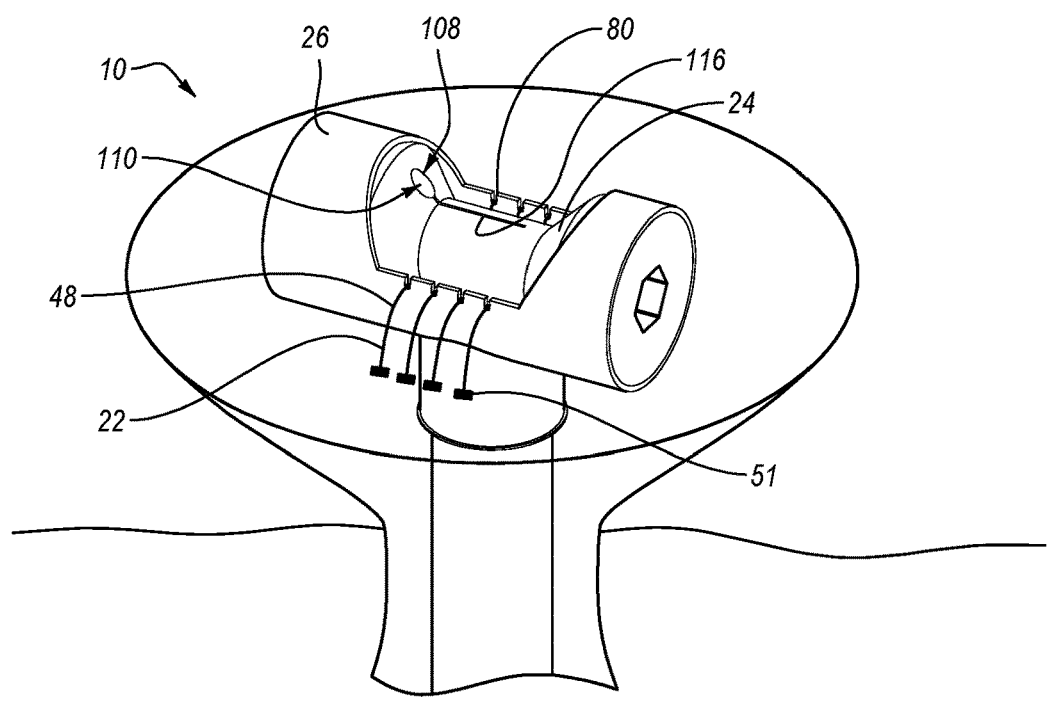

Barrel member 60 can also comprise an upper operating opening 66 providing access into receiving area 64 (e.g., opposite stem 62). For instance, in certain implementations, operating opening 66 can be (180°) opposite stem 62, access opening 68, and/or lower distal opening 74. In at least one implementation, barrel member 60 can also include one or more (e.g., a plurality of) connection elements 80 disposed adjacent to receiving area 64. For instance, connection elements 80 can comprise one or more notches extending into barrel member 60 from operating opening 66. Connection elements 80 can be adapted and/or configured (e.g., sized) to secure wires 22 therein, such as by a pressure fit (see e.g., FIG. 8B). For instance, the notches can have a thickness such that wires 22 may be secured tightly and/or easily within the notches and/or such that wires 22 do not, cannot, and/or may not loosen unless manually adjusted by a user. In one or more implementations, housing 26 can include one or more elongated handles extending therefrom, such as from opening 76, 78, or a portion of barrel member 60 adjacent thereto.

Housing 26 can comprise and/or be formed of a variety of (surgical-grade) materials, including plastics or polymers, such as acrylonitrile-butadiene-styrene (ABS), poly(vinyl chloride) (PVC), and the like. Other materials such as polymer resins, epoxies, metals, and/or metal alloys, or combinations of any of the foregoing or other materials can also be suitable for forming housing 26, and are contemplated herein. The material of housing 26, including barrel member 60 and/or stem 62 thereof, can also have any suitable thickness, strength, rigidity, or other property. For instance, housing 26, or barrel member 60 and/or stem 62 thereof, can have a substantially rigid and/or sturdy configuration (e.g., without any substantial degree of flexibility or elasticity).

Housing 26 can also have any suitable thickness, such as between outer surface 61 and inner surface 63 of barrel member 60 and/or outer surface 64 and inner surface 67 of stem 62. For instance, the thickness of housing 26, barrel member 60, and/or stem 62 can be between about 1 mm and about 10 mm, preferably between about 2 mm and about 5 mm, more preferably between about 3 mm and about 4 mm. In at least one implementation, housing 26 can have a substantially uniform thickness, such that the thickness of barrel member 60 is substantially similar to the thickness of stem 62. In other implementations, however, barrel member 60 can have a thickness that is greater than the thickness of stem 62, or vice versa. Moreover, in certain implementations, the thickness of housing 26 at one or more proximal portions can be greater than the thickness of housing 26 at one or more distal portions, or vice versa. For instance, the thickness of housing 26 adjacent to access opening 68 can be greater than the thickness of housing 26 at open end(s) 76, 78 of barrel member 60 and/or distal opening 74 of stem 62.

Figure 5A:
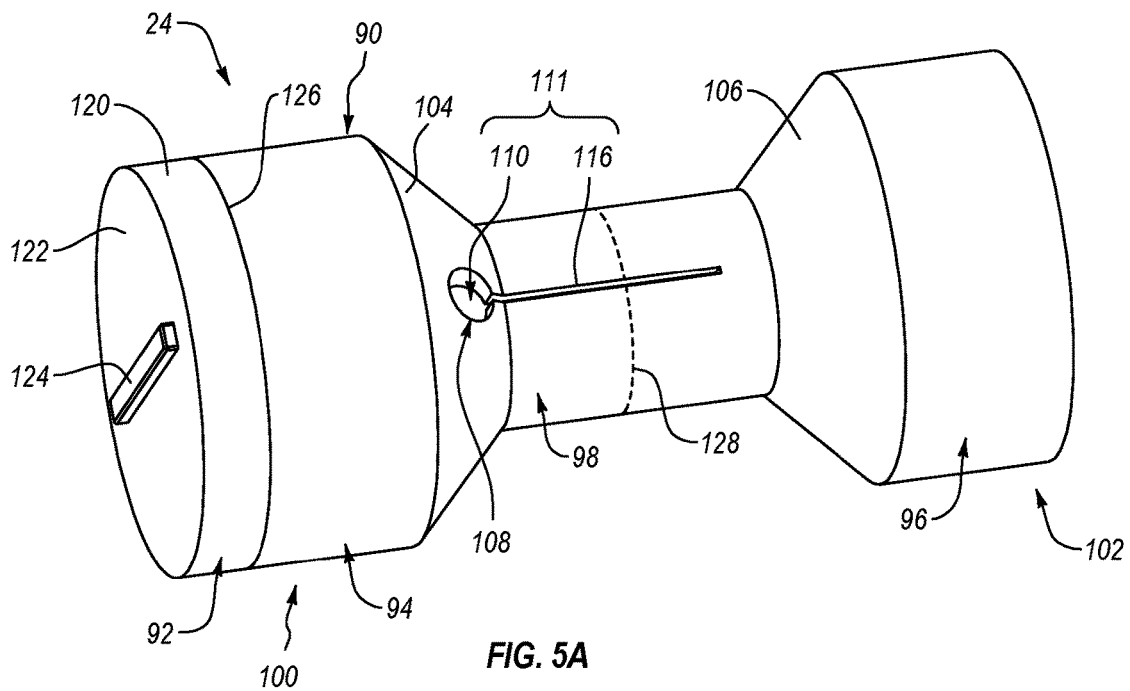
FIGS. 5A-5B illustrate perspective views of a retracting element in accordance with an implementation of the present disclosure.
Figure 5B:
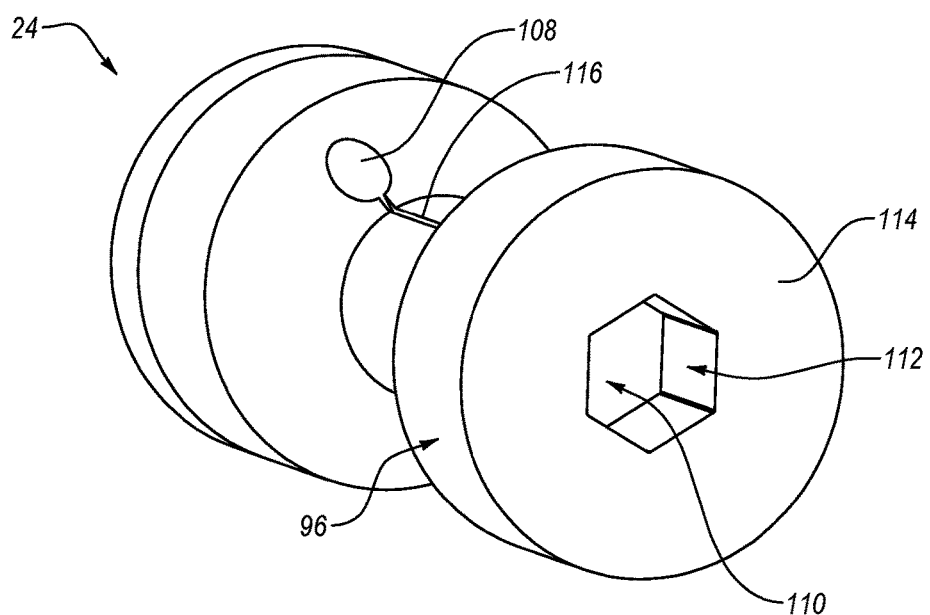

FIG. 5A and FIG. 5B depict opposing views of an exemplary wire retracting element 24. The wire retracting element 24 can be sized, shaped, and/or configured to fit (securely, but not tightly) within housing 26, barrel 60, and/or receiving area 64 thereof. As illustrated in the depicted implementation, for instance, at least a portion of retracting element 24 can have a substantially cylindrical configuration. More particularly, retracting element 24 (or a spool 90 thereof) can have a substantially V-shaped, hour-glass-shaped, and/or dumbbell shaped (at least partially recessed) configuration and/or resemble the shape thereof, or have another at least partially recessed configuration. As described in further detail below, wires 22 that are wrapped around retracting element 24 can be collected to a central or middle portion of wire retracting element 24. It will be appreciated, however, that retracting element 24 can also or alternatively be of have a non-cylindrical configuration without necessarily departing from the scope of the present disclosure.

Retracting element 24 can comprise a spool 90 and, optionally, a ratcheting element 92 attached to a first end 100 of spool 90. Spool 90 can comprise a first body portion 94, a second body portion 96 (e.g., opposite first body portion 94), and a collection member 98 (e.g., disposed between first body portion 94 and second body portion 96). First body portion 94 can be disposed at first end 100 and second body portion 96 can be disposed at second end 102 (e.g., opposite first end 100).

As further illustrated in the depicted implementation, first body portion 94, second body portion 96, and/or collection member 98 can have a substantially cylindrical configuration. In at least some implementations, at least a portion of collection member 98 can be smaller than first body portion 94 and/or second body portion 96. For instance, at least a portion of collection member 98 can have a diameter and/or circumference that is substantially or at least partially smaller (or less) then the diameter and/or circumference of first body portion 94 and/or second body portion 96. In one or more implementations, retracting element 24 can also include a sloped, chamfered, or beveled surface disposed between first body portion 94 and collection member 98 and/or between second body portion 96 and collection member 98. For instance, FIG. 5A illustrates a first slope, chamfer, or bevel 104 disposed between first body portion 94 and collection member 98 and a second slope, chamfer, or bevel 106 disposed between second body portion 96 and collection member 98.

As further illustrated in the depicted implementation, retraction element 24 and/or one or more portions thereof (e.g., first slope, chamfer, or bevel 104 and/or second slope, chamfer, or bevel 106) can include a securing mechanism 111. As depicted in FIG. 5A, securing mechanism 111 can include at least one opening or aperture 108 disposed on or in and/or extending through retracting element 24 and/or one or more portions thereof (e.g., first slope, chamfer, or bevel 104 and/or second slope, chamfer, or bevel 106). In certain implementations, first slope, chamfer, or bevel 104 and second slope, chamfer, or bevel 106 can each comprise an opening or aperture 108 (see e.g., FIG. 6; openings or apertures 108a, 108b).

Opening or aperture 108 can communicate with an internal cavity 110 of retracting element 24 and/or one or more portions thereof. Internal cavity 110 can extend through collection member 98, (e.g., from first slope, chamfer, or bevel 104 to second slope, chamfer, or bevel 106). In at least some implementations, internal cavity 110 can extend (at least partially) through first slope, chamfer, or bevel 104 and/or second slope, chamfer, or bevel 106. In certain implementations, internal cavity 110 can extend (at least partially) through first body portion 94 and/or second body portion 96. Accordingly, in at least one implementation, spool 90 can be substantially hollow and configuration and/or construction. As described in further detail below, connection components 51 from the ends of the wires 22 can be attached to spool 90, such as by insertion through opening or aperture 108 and into internal cavity 110.

FIG. 5A further shows that retracting element 24 and/or one or more portions thereof can also include at least one slot (or slit) 116. Slot 116 can comprise an elongated opening extending from opening 108. For instance, in the depicted implementation, slot 116 can comprise an elongated opening extending substantially linearly (relative to the line extending from first end 100 to second end 102) from opening 108 toward second end 102. In an alternative implementation, however, one or more slots can extend diagonally (relative to the line extending from first end 100 to second end 102) from opening 108 toward middle line 128 (see e.g., FIG. 6; slots 116a, 116b).

As described in further detail below, slot 116 can be adapted to direct wires 22 toward the center of spool 90 (e.g., to facilitate the wrapping of wires 22 around the center of spool 90. The substantially V-shaped, hourglass-shaped, and/or dumbbell shaped (at least partially recessed) configuration of school 90 can facilitate wires 22 wrapping around a central or middle portion of spool 90. Opening(s) 108 can also be placed at peripheral or distal end(s) of spool 90, so as to prevent wires 22 from wrapping around opening(s) 108, where additional connection components 51 of wire(s) 22 (or ends 44, 46 thereof) can be placed (e.g., in order to wrap multiple wires 22 around or about spool 90.

As illustrated in FIGS. 5A-5B, slot 116 can extend from opening 108 at least partially through first slope, chamfer, or bevel 104 and/or into collection member 98 (e.g., but not entirely to or into second slope, chamfer, or bevel 106. In certain implementations, however, slot 116 can extend entirely through collection member 98 (e.g., to the interface between collection member 98 and second slope, chamfer, or bevel 106). In at least one implementation, slot 116 can extend only partially through first slope, chamfer, or bevel 106 (see e.g., FIG. 6; slots 116a, 116b). Slot 116 can also communicate with internal cavity 110.

In at least one alternative implementation, securing mechanism 111 can comprise one or more hooks, anchors, protrusions, or other feature (e.g., disposed on the surface of retraction element 24). As described in further detail below, securing mechanism 111 can be adapted and/or configured to receive one or more securing elements, such as securing elements 51 (e.g., disposed on the end(s) of wires 22).

As depicted in FIG. 5B, second body portion 96 can include an opening 112 (e.g., disposed at an outer (peripheral or distal) end (e.g., surface or face) 114 thereof and/or at second end 102 of retracting element 24). In at least one implementation, opening 112 can communicate with internal cavity 110. It will be appreciated, however, that retracting element 24 and/or second body portion 96 thereof can include opening 112 without an internal cavity 110 extending through retracting element 24 and/or one or more portions thereof. Opening 112 can extend at least partially through second body portion 96. As illustrated in the depicted implementation, opening 112 can also have a hexagonal shape or configuration. It will be appreciated, however, that opening 112 can have any suitable shape or configuration, including rectangular, triangular, pentagonal, hexagonal, heptagonal, octagonal, starred (star-shaped or star-pattern), or other shape or configuration. Opening 112 can be configured to receive an attachment component of ratcheting (socket) wrench or other rotating (handle) element (see e.g., handle 93 of FIG. 6). In at least some implementations, first body portion 94 can have an opening similar to opening 112.

As illustrated in the depicted implementation, spool 90 can have a unitary and/or (substantially) seamless configuration. Accordingly, spool 90 can be formed as a single and/or unitary piece.

In an alternative implementation, however, spool 90 can be formed of separate (substantially similar and/or mirror symmetrical) school elements. For example, a first spool element can comprise first body portion 94, first slope, chamfer, or bevel 104, and a portion (e.g., half) of collecting member 98 (e.g., as indicated by line 128). Similarly, a second spool element can comprise a second body portion 96, second slope, chamfer, or bevel 106, and a portion (e.g., half) of collecting member 98 (e.g., as indicated by line 128).

An attachment mechanism can secure the first spool element to the second spool element. For instance, a first connection component, such as a male threaded member can extend from the first spool element and or the portion (e.g., half) of collecting 98 thereof (e.g., adjacent line 128) and a second connection component, such as a female threaded member can extend from the second spool element and or the portion (e.g., half) of collecting member 98 thereof (e.g., adjacent line 128). Accordingly, the first and second spool elements can be threadedly secured together, thereby forming spool 90. In such a configuration, retracting element 24 may not include a ratcheting element 92 attached, connected, and/or secured thereto.

As illustrated in the depicted implementation, first body portion 94 has a ratcheting element 92 attached to the outer (peripheral or distal) end (e.g., surface or face) thereof. A seam and/or connection interface 126 can be disposed and/or formed between spool 90 and a ratcheting element 92. In at least one implementation, ratcheting element 92 can comprise a thumbwheel ratchet or other mechanism for permitting selective rotation in one or more rotational directions. Ratcheting element 92 can have a cylindrical or disc-shaped configuration or shape, with a (rounded, circumferential) edge 120 and/or a (substantially flat) outer (peripheral or distal) end (e.g., surface or face) 122. In an alternative implementation, however, ratcheting element 92 and/or edge 120 thereof can be or have a non-cylindrical shape or configuration. For instance, ratcheting element 92 and/or edge 120 thereof can have or comprise an oval, rectangular, triangular, pentagonal, hexagonal, heptagonal, octagonal, or other shape or configuration.

In one or more implementations, ratcheting element 92 and/or edge 120 thereof can have a diameter (or other cross-sectional measurement) and/or circumference (or other outer surface measurement) that is (substantially or at least partially) larger than and/or extends (substantially or at least partially) beyond the diameter (or other cross-sectional measurement) and/or circumference (or other outer surface measurement) of spool 90 and/or the first body portion 94 and/or second body portion 96 thereof. Accordingly, seam and/or connection interface 126 disposed and/or formed between spool 90 and a ratcheting element 92 can comprise a lip, ramp, chamfer, bevel, slope, or step in certain implementations.

Ratcheting element 92 can be connected to the spool 90 such that spool 90 can rotate (e.g., clockwise and/or counterclockwise) relative to ratcheting element 92. For instance, ratcheting element 92 can also include a (rotational direction) selector 124. In at least one implementation, manipulation of selector 124 can permit and/or inhibit rotation of spool 90 relative to ratcheting element 92 in a clockwise and/or counterclockwise direction.

The ratcheting system of retraction element 24 can optionally include a (second) ratcheting element 92 disposed on the opposite side of spool 90 (e.g., to facilitate a faster winding of the wire. A handle, such as a handle 93 of FIG. 6, can also be integrated into the side of spool 90 (e.g., in order to provide counter traction when ratcheting spool 90 and/or to prevent spool 90 from unwinding (e.g., prior to full segmentation of the tissue), as described in further detail below. The handle can also be removable in certain implementations. Mechanical teeth of different forms may also be integrated into housing 26 and/or spool 90 to prevent the unintentional unwinding of spool 90.

Retracting element 24, spool 90, and/or ratcheting element 92 can comprise and/or be formed of a variety of (surgical-grade) materials, including plastics or polymers, such as acrylonitrile-butadiene-styrene (ABS), poly(vinyl chloride) (PVC), and the like. Other materials such as polymer resins, epoxies, metals, such as aluminum, metal alloys, and/or any suitable combination of any of the foregoing or other materials can also be suitable for forming retracting element 24, spool 90, and/or ratcheting element 92, and are contemplated herein. The material of retracting element 24, spool 90, and/or ratcheting element 92 can also have any suitable thickness, strength, rigidity, or other property, and can have a substantially rigid and/or sturdy configuration (e.g., without any substantial degree of flexibility or elasticity).

Returning to FIG. 3, and with continued reference to FIG. 4 and FIG. 5A, retracting element 24 and/or spool 90 thereof can be rotationally and/or rotatably disposed (e.g., secured) within housing 26 and/or receiving area 64 thereof. For instance, the diameter (or other cross-sectional measurement) and/or circumference (or other outer surface measurement) of spool 90 can be (slightly) smaller than the diameter (or other cross-sectional measurement) and/or circumference (or other outer surface measurement) of barrel member 60 and/or receiving area 64. It will also be appreciated that spool 90 can, in certain implementations, fit into a housing 26, such that friction between spool 90 and housing 26 can be minimized, so as to allow a maximum mechanical advantage when the spool is turned and/or rotated (e.g., using ratcheting element 92) within housing 26.

In the depicted implementation, ratcheting element 92 can be pressure fit into housing 26, barrel member 60, and/or receiving area 64 thereof. Accordingly, where spool 90, a first body portion 94, and/or second body portion 96 are at least partially smaller than ratcheting element 92 and/or edge 120 thereof, spool 90 can be rotationally and/or rotatably disposed within housing 26 and/or receiving area 64 thereof, while ratcheting element 92 is non-rotationally and/or non-rotatably disposed within and/or rotationally and/or rotatably fixed relative to housing 26 and/or receiving area 64 thereof.

In certain implementations (e.g., where spool 90 is formed of more than one spool element), housing 26 and/or barrel member 60 thereof may include one or more lips, ramps, chamfers, bevels, slopes, or steps (e.g., extending into receiving area 64) that prevent and/or inhibit spool 90 from exiting receiving area 64 (e.g., without first separating the (opposing) spool elements).

FIG. 6 illustrates an alternative implementation of a retracting element 24a. Retracting element 24a can be substantially similar to retracting element 24, with one or more differences as depicted in FIG. 6 and described herein. For instance, retracting element 24a can include a first spool element 160, comprising a first slope, chamfer, or bevel 104a extending from a first body portion 94a, and a second spool element 162, comprising a second first slope, chamfer, or bevel 106a will extending from a second body portion 96a. Unlike retracting element 24, retracting element 24a does not include a collection member 98. Instead, first slope, chamfer, or bevel 104a and second first slope, chamfer, or bevel 106a can be joined at connection interface 128a (e.g., by means of an attachment mechanism comprising a first connection component 150, such as a male threaded member and/or a second connection component 152, such as a female threaded member. It will be appreciated, however, that first and second connection components 150, 152 can alternatively form a snap fit, locking fit, or other attachment mechanism.

First slope, chamfer, or bevel 104a comprises a first opening or aperture 108a and a first slit (or slot) 116a extending diagonally therefrom (relative to the line extending from first body portion 94a to second body portion 96a) from opening 108a toward connection interface 128a. Similarly, second slope, chamfer, or bevel 106a comprises a second opening or aperture 108b and a second slit (or slot) 116b extending diagonally therefrom (relative to the line extending from first body portion 94a to second body portion 96a) from opening 108b toward connection interface 128a. Retracting element 24a also includes a handle member 93 (e connected to and/or extending from second body portion 96a and/or a ratcheting element 92a (e.g., connected to handle member 93 and/or second body portion 96a.

FIG. 7A and FIG. 7B depict an exemplary (tubular) positioning member 28. The positioning member 28 can have a tubular and/or substantially cylindrical configuration, with a (substantially cylindrical) outer surface 130 and a (substantially cylindrical) inner surface 132 extending from a first end 136 to a second end 138 opposite first end 136. It will be appreciated, however, that positioning member 28, outer surface 130, and/or inner surface 132 can also or alternatively be non-cylindrical (e.g., and still be tubular in nature). For instance, positioning member 28, outer surface 130, and/or inner surface 132 can have or comprise an oval, rectangular, triangular, pentagonal, hexagonal, heptagonal, octagonal, or other shape or configuration.

Inner surface 132 can at least partially bound a conduit 134 extending from first end 136 to second end 138. First end 136 can have an opening 140 in communication with conduit 134. Second end 138 can have an opening 142 in communication with conduit 134. Conduit 134 can have any suitable diameter, circumference, and/or cross-sectional measurement. For instance, the diameter of positioning member 28 and/or conduit 134 thereof can be small or large and may range from 0.5 cm in diameter up to 5 cm or more. The limit to the diameter of positioning member 28, in certain implementations, can be determined based upon the size of a surgical incision (e.g., vaginal or abdominal).

In alternative implementations, the positioning member 28 can be replaced by a (minimally invasive, such as laparoscopic, or other) surgical port. The surgical port can (also) have one or more different uses or functions during a minimally invasive surgery. For instance, in at least one implementation, a surgical port can be provided to secure opening 34 and/or forming element 54 thereof at or adjacent to the surgical incision. The surgical port piece can, therefore, double as a positioning member for introducing wires 22 from bag 20 into retraction assembly 18, and also or alternatively, introducing surgical instruments into the surgical cavity (e.g., abdomen) as traditionally used in minimally invasive (or laparoscopic) surgery.

In addition, positioning member 28 can have any suitable length extending from first end 136 to second end 138. In at least one implementation, for instance, positioning member 28 can have a length between about 1 cm and about 50 cm, preferably between about 2 cm and about 30 cm, more preferably between about 2 cm and about 20 cm, or between about 5 cm and about 10 cm, extending from first end 136 to second end 138.

FIG. 7b further shows that positioning member 28 can also include a connection component 144. Connection component 144 can comprise a flange and/or extension extending from outer surface 130. With additional reference to FIG. 1, FIG. 3, and FIG. 4, connection component 114 can be configured to attach to retraction assembly 18, housing 26, and/or stem 62 (e.g., at or adjacent to a lower distal opening 74 thereof). For instance, an upper portion of positioning member 28 (adjacent to first end 136) can fit within opening 74 and/or into accessed channel 70, such as by means of a pressure fit. Connection component 114 can comprise a flange that indicates a proper positioning of positioning member 28 and/or provides a backstop or wall for the connection thereof to housing 26.

In an alternative implementation, however, connection component 114 can comprise one or more threads (or threadings). Accordingly, interior surface 67 of stem 62 can have corresponding threads (or threadings) disposed thereon. Thus, positioning member 28 can be threadedly connected to retraction assembly 18, housing 26, and/or stem 62. In the attached configuration illustrated in FIG. 1, FIG. 7A, and FIG. 7B, conduit 134 of positioning member 28 can be in communication with access channel 70 of housing 26 and/or stem 62 thereof, and/or receiving area 64 of housing 26 and/or barrel member 60 thereof.

In at least one implementation, tissue retrieval device 10 can also have or include means for applying an electrical current to wires 22 connected thereto and/or associated there with. Accordingly, in addition to mechanical forces provided by the rotation of retraction element 24 within housing 26, wires 24 can function as an electrosurgical wires, which can electro-surgically cut, slice, or sever through tissue sample 8.

Methods

An illustrative method of assembling a tissue retrieval device, such as tissue retrieval device 10 depicted in FIG. 1, can comprise providing a housing, such as housing 26 and a retraction element, such as retraction element 24. Retraction element 24 can be inserted into and/or disposed within housing 26 and/or receiving area 64 thereof. For instance, a unitary retraction element 24 can be inserted through one of openings 76 or 78. Ratcheting element 92 can be pressure fit into housing 26, such that ratcheting element 92 is fixed relative to housing 26 and spool 90 is rotatably and/or rotationally disposed within receiving area 64.

Alternatively, a two-piece retraction element 24 can be assembled inside of receiving area 64. For instance a first spool element, such as first spool element 160, can be inserted (connection component 150, first) through first opening 76 of housing 26, and a second spool element, such as second spool element 162, can be inserted (connection component 152, first) through second opening 78 of housing 26. The first and second spool elements can then be connected and/or secured together by means of the attachment mechanism thereof at a connection interface, such as connection interface 128, 128a. An optional positioning member, such as positioning member 28, can be optionally attached to retraction assembly 18, housing 26, and/or stem 62 (e.g., by means of a pressure fit within accessed channel 70 and/or by means of a connection component 144, with a corresponding connection component of retraction assembly 18, housing 26, and/or stem 62).

Retraction assembly 18 can be connected to bag assembly 16 as depicted in FIG. 1, FIG. 7A, and FIG. 7B. For instance, stem 62, or optional positioning member 28, can be inserted at least partially into compartment 40 of bag 20 by means of opening 34. As illustrated in the depicted implementation, positioning member 28 can be inserted into compartment 40. Wires 22 and/or extensions 48, 50 thereof, can be inserted through lower opening 142 of positioning member 28, through conduit 134 thereof, through accessed channel 70 of stem 62, through receiving area 64, and, optionally, out through the access opening 66, as illustrated in FIG. 7A. Wires 22 can also be placed into a holding position or configuration within connection elements 80, as illustrated in FIG. 7B.

Securing elements 51 can be inserted (sequentially) through opening or aperture 108, such that securing elements 51 are inserted into internal cavity 110 of spool 90. Wires 22 and/or extensions 48, 50 thereof can be slid into slit (or slot) 116, becoming securely retained therein. For instance, securing elements 51 of a last overlaid wire 22 (e.g., with a first sequential indicator disposed thereon, such as on securing element 51), can be inserted into opening 108 as a first wire attaching step. Similarly, securing element 51 of a second-to-last overlaid wire 22 (e.g., with a second sequential indicator disposed thereon, such as on securing element 51), can be inserted into opening 108 as a second wire attaching step, and so forth. Likewise, a securing element 51 of a first later wire 22 (e.g., with a last sequential indicator disposed thereon, such as on securing element 51), can be inserted into opening 108 as a last (or final) wire attaching step.

In an alternative implementation, however, all wires 22 and/or securing element 51 thereof need not be inserted into opening 108. Indeed, certain methods can include inserting and/or otherwise attaching at least one and of a wire 22 to retraction element 24. In another alternative implementation, wires 22, ends 44, 46 thereof, and/or extensions 48, 50 thereof, can be inserted through positioning member 28 and into housing 26 prior to disposing retracting element 24 within receiving area 64. For instance, wires 22 can be fed through retracting element 24 and secured within connection elements 80 of housing 26. Retraction element 24 can then be disposed (e.g., inserted and/or assembled) within receiving area 64. Wires 22 can then be connected to retracting element 24 as described above.

In view of the foregoing, one will appreciate that implementations of the present invention can further include one or more methods of tissue extraction. For example, one exemplary method of removing tissue from a patient body in accordance with the present disclosure can include, in any suitable order or sequence, providing a bag assembly, such as bag assembly 16, making a surgical incision or cut in the patient body, optionally detaching a tissue to be removed from within the patient body, collapsing the bag assembly into a collapsed configuration, and/or inserting the collapsed bag assembly through the surgical incision and into a surgical cavity of the patient. The bag can be malleable, so as to extend through a restricted size of the (minimally-invasive) surgical opening. In at least one implementation, the surgical incision can comprise a laparoscopic or other minimally invasive incision in the outer (dermal) body of the patient. In other implementations, the surgical incision can comprise an opening, such as a vaginal cervical opening (e.g., opening in the distal end of the vagina) within the patient body. In some implementations, the surgical incision can be formed by separating the tissue to be removed from the patient body.

In certain implementations, the method can also include inserting a tissue to be removed into a bag, such as bag 20, of the bag assembly (e.g., through an opening, such as opening 34, thereof). The opening of the bag can also extend outside of the patient body. For instance, the opening can (then) be pulled through the surgical opening, such that the opening of the bag extends outside of the patient body. As described above, the bag assembly can also include one or more wires, such as wires 22, attached to the interior surface of the bag. The wires can be secured to the (internal surface) of the bag by means of one or more attachment mechanisms, such as attachment mechanism 53 (e.g., comprising an adhesive and/or overlay, such as one or more rings, loops, anchors, staples, sutures, sheets, or layers (e.g., of film)).

The method can include connecting the one or more wires to a wire retracting element, such as wire retracting element 24. Wire retracting element 24 can be rotatably disposed within and/or attached to a housing, such as housing 26.

The method can also include a rotating the wire retracting element relative to the housing, such that a first portion of the wire(s), such as one or more extensions 48, 50, are wound about the wire retracting element and a second portion of the wire, such as at least part of middle portion 53, detaches from the interior surface and contacts the tissue. In some implementations, a tubular positioning member, such as positioning member 28, can extend from (a lower portion) of housing 26, such as stem 62. The wires can pass through a conduit 134 extending through the tubular positioning member, through and access channel, such as accessed channel 70, stem 62, through and access opening, such as access opening 68, and/or into a receiving area, such as receiving area 64, of housing 26. The wires can also be connected to a connection element, such as connection elements 80 (e.g., while the retracting element is inserted and/or assembled within the housing and/or receiving area thereof.

The wire(s) can also have a securing element, such as securing element 51 (e.g., disposed at one or more ends thereof). The securing elements can be connected to a securing mechanism, such as securing mechanism 111, of the retracting element. For instance, the securing element(s) of the wire(s) can be inserted through an opening, such as opening 108, in the securing element and into an internal cavity thereof, such as internal cavity 110. The wires can also be slid into a slot, such as slot 116, such that the securing elements to not become inadvertently separated from the retracting element. In an alternative implementation, the securing mechanism can comprise one or more hooks, anchors, protrusions, or other feature (e.g., disposed on the surface of retraction element 24), and the securing element(s) can comprise a ring, loop, or other attachment member configured for securing wire 22 (e.g., in a hook-and-loop fashion) to the securing mechanism. Accordingly, the securing element(s) can also or alternatively be attached and/or hooked to (a securing mechanism disposed on) the surface of the securing element.

Rotation of the retracting element relative to the housing can wind or wrap the wire(s) around or about the retracting element, drawing the wire(s) up through the optional positioning member and into housing 26, thereby tightening the wire(s) around the tissue sample disposed within the bag, inside the patient body. The retracting element can be rotated by means of a handle, such as handle 93, or other means for rotating, such as a (ratcheting and/or socket) wrench (e.g., as known in the art). In at least one implementation, for example, rotation of the retracting element can produce a (pulling) force on the wires that separates and/or detaches at least a portion of the wires from the internal surface of the bag. In some implementations, a fluid, solvent, or other component (e.g., within the surgical cavity and/or introduced (directly and/or indirectly) into the bag or internal compartment thereof) can dissolve, week in, and/or otherwise structurally modified the (integrity of) the attachment mechanism (securing the wires to the (internal surface of) the bag. Alternatively, the force produced by rotation of the retracting element can be sufficient to disassociate the wires from the bag.

Continued rotation of the wire retracting element relative to the housing can cause or result in the wire(s) passing through the tissue, thereby sectioning the tissue to be removed. The optional positioning member can (1) provide (back) pressure (in a direction opposite the direction of the wire retraction direction into the housing) against the tissue during the continued rotation, and/or (2) help to maintain an orientation of the tissue during sectioning. Securing the mass in place can be very useful, helpful, and/or important for effective segmentation of the tissue as well as for maintaining the orientation of the mass, as described above. Thus, the position member can provide pressure on the tissue mass within the surgical cavity (e.g., abdomen) as the wires put force on the mass, both to secure the mass in place and to segment the tissue. The position member can also serve the purpose of providing the path through which the wires are directed to the spool. The bag, on the other hand, can be disposed outside the position member.

The sectioned portions of the tissue can then be removed through the opening in the (liquid-impermeable) bag, which may be disposed outside the patient body (e.g., such that any (unknown and/or undiagnosed) cancerous, viral, bacterial, fungal, or other material(s) and/or components are (or can be) spread within the surgical cavity).

Various alterations and/or modifications of the inventive features illustrated herein, and additional applications of the principles illustrated herein, which would occur to one skilled in the relevant art and having possession of this disclosure, can be made to the illustrated implementations without departing from the spirit and scope of the invention as defined by the claims, and are to be considered within the scope of this disclosure. Thus, while various aspects and implementations have been disclosed herein, other aspects and implementations are contemplated. While a number of methods and components similar or equivalent to those described herein can be used to practice implementations of the present disclosure, only certain components and methods are described herein.

It will also be appreciated that systems, processes, and/or products according to certain implementations of the present disclosure may include, incorporate, or otherwise comprise properties features (e.g., components, members, elements, parts, and/or portions) described in other implementations disclosed and/or described herein. Accordingly, the various features of certain implementations can be compatible with, combined with, included in, and/or incorporated into other implementations of the present disclosure. It will be understood that changes may be made in the function and arrangement of elements discussed without departing from the spirit and scope of the disclosure, and various implementations may omit, substitute, or add other procedures or components as appropriate. For instance, the methods described may be performed in an order different from that described, and various steps may be added, omitted, or combined.

Thus, disclosure of certain features relative to a specific implementation of the present disclosure should not be construed as limiting application or inclusion of said features to the specific implementation. Rather, it will be appreciated that other implementations can also include said features without necessarily departing from the scope of the present disclosure. Moreover, unless a feature is described as requiring another feature in combination therewith, any feature herein may be combined with any other feature of a same or different implementation disclosed herein. Furthermore, various well-known aspects of illustrative systems, processes, products, and the like are not described herein in particular detail in order to avoid obscuring aspects of the example implementations. Such aspects are, however, also contemplated herein.

The present disclosure may be embodied in other specific forms without departing from its spirit or essential characteristics. The described implementations are to be considered in all respects only as illustrative and not restrictive. The scope of the invention is, therefore, indicated by the appended claims rather than by the foregoing description. Each of the appended claims, as well as the recited elements thereof, is intended to be combinable with any other claim(s) and/or element(s) in any suitable combination or dependency without regard to the dependency in which said claims are presented. While certain implementations and details have been included herein and in the attached disclosure for purposes of illustrating implementations of the present disclosure, it will be apparent to those skilled in the art that various changes in the methods and apparatus disclosed herein may be made without departing from the scope of the invention, which is defined in the appended claims. All changes which come within the meaning and range of equivalency of the claims are to be embraced within their scope.

We claim:

1. A method of removing tissue from a body, the method comprising:
    inserting a collapsible bag through a surgical opening, the bag including
        an opening disposed at a first end and a closed bottom disposed at a second end opposite the opening, and
        a plurality of wires attached to and extending along an interior surface of the bag and having wire ends extending beyond the opening of the bag,
        wherein the wires along the interior surface of the bag each intersect one another at a defined crossover point disposed at the second end of the bag;
    inserting a tissue to be removed into the bag;
    positioning the bag so that the bag opening and wire ends extend outside of the surgical opening while a remainder of the bag holding the tissue to be removed remains inside of the surgical opening;

after positioning the bag, routing the wire ends through a distal end of a tubular positioning member, the tubular positioning member being attached to a housing at a proximal end;

connecting the wire ends to a slotted wire retracting element, the wire retracting element being configured to securely receive the wire ends and being moveable relative to the housing to produce a pulling force on the wires; and moving the wire retracting element relative to the housing so as to pull the wires through the tubular positioning member to cause the wires to detach from the interior surface of the bag, including causing the wires at the defined crossover point at the second end of the bag to detach from the interior surface of the bag; and pulling the wires further so that the tissue contacts the distal end of the tubular positioning member and so that the wires move through the tissue to segment the tissue.

2. The method of claim 1, wherein the housing comprises:
a receiving area and an access opening in communication with the receiving area,
wherein the wire retracting element is a spool rotatably disposed within the receiving area, the wire ends extending from the bag, through the tubular positioning member, and through the access opening to the receiving area.

3. The method of claim 1, wherein the positioning member provides pressure against the tissue as the wires pull against and through the tissue.

4. The method of claim 1, further comprising removing a sectioned portion of the tissue.

5. The method of claim 1, wherein inserting the bag comprises collapsing the bag such that the collapsed bag fits through a surgical incision, and wherein the bag is flexible and liquid-impermeable.

6. A tissue removal device comprising:
a flexible, liquid-impermeable bag having an interior surface extending from a first end of the bag to a second end of the bag, the interior surface at least partially bounding a tissue compartment,
wherein the first end has an opening formed therein, the opening communicating with the compartment, and
wherein the second end is opposite the first end, the second end having a closed bottom;
a plurality of wires attached to the bag, each wire extending along the interior surface from a first portion of the opening to a second portion of the opening opposite the first portion by extending downward from the first portion of the opening, along the closed bottom, and upward to the second portion of the opening,
wherein the wires intersect one another at a defined crossover point at the second end of the bag,
wherein each wire comprises a first extension protruding beyond the first portion of the opening and a second extension protruding beyond the second portion of the opening,
wherein the bag defines a longitudinal direction extending through the compartment from a center of the closed bottom to a center of the opening, and
wherein the first and second extensions of each wire protrude from the first portion of the opening in the longitudinal direction; and
a releasable fastener disposed in the compartment, wherein the releasable fastener is adapted to maintain an orientation of the wires along the interior surface in the absence of a detaching force, and allow the wires to detach from the interior surface upon exposure of the wires to a detaching force, including allowing the wires at the defined crossover point at the second end of the bag to detach from the interior surface upon exposure of the wires to a detaching force.

7. The tissue removal device of claim 6, further comprising:
a ring-shaped wire collection mechanism connected to the first end of the bag and connected to each wire along the bag opening,
wherein the first and second extensions extend proximally from the wire collection mechanism.

8. The tissue removal device of claim 6, wherein the releasable fastener comprises one or more fasteners selected from the group consisting of:
a covering connected to the interior surface and extending over at least a portion of each of the wires, such that the portion of each of the wires is disposed between the interior surface and the covering, the covering comprising one or more rings, loops, anchors, staples, sutures, or layers of film; and
an adhesive disposed on at least a portion of the interior surface, the wires being attached to the portion of the interior surface by means of the adhesive.

9. The tissue removal device of claim 6, further comprising:
a slotted wire retracting element attached to a housing, wherein the wire retracting element is adapted to secure the first and second extension of each wire and enable retraction of each wire by moving relative to the housing.

10. The tissue removal device of claim 9, wherein the housing comprises a receiving area and an access opening in communication with a portion of the receiving area,
wherein the wire retracting element is a spool rotatably disposed within the receiving area, such that rotation of the wire retracting element relative to the housing winds the wires about the wire retracting element.

11. The tissue removal device of claim 9, wherein the housing further comprises a tubular positioning member extending distally from an access opening of the housing,
wherein the positioning member comprises a channel communicating with the access opening, and
wherein the first and second extension of each wire extend through the channel, through the access opening, and into a receiving area of the housing.

12. A tissue removal device comprising:
a bag having an interior surface, an opening at a first end, and a closed second end opposite the opening, the bag defining a longitudinal axis extending from the closed second end to a center of the opening;
a wire assembly that includes a plurality of wires detachably connected to the interior surface of the bag, each wire extending along a side portion of the bag in a distal longitudinal direction, along the second end of the bag, and along a directly opposite side portion of the bag in a proximal longitudinal direction, each wire thereby symmetrically bisecting the bag,
wherein the wires intersect one another at a defined crossover point disposed at the second end of the bag,
wherein opposing ends of at least one wire have matching indicators to indicate opposing ends of the same wire, and wherein the wires extend proximally beyond the opening of the bag to form wire extensions terminating in wire ends;

a tubular positioning member having a conduit through which the wire extensions pass;

a housing attached to a proximal end of the tubular positioning member; and a slotted wire retraction element disposed within the housing, the wire retraction element being configured to receive the terminal wire ends and being moveable relative to the housing and tubular positioning member to provide a proximal pulling force on the wires.

13. The device of claim 12, wherein the wire crossover point is disposed directly opposite the distal end of the tubular positioning member.

14. The device of claim 12, wherein the wire crossover point is the only point along the interior surface of the bag where the wires intersect.

15. The device of claim 12, further comprising a forming element integrated into the opening of the bag to give form to the opening of the bag, the forming element including a wire lasso lining the opening of the bag and being connected to each wire at the opening of the bag.

16. The device of claim 12, wherein the opening of the bag is detached from the tubular positioning member.

17. The device of claim 12, wherein multiple wires include indicators and wherein the indicators are sequentially labelled to indicate an overlay order of each wire.

18. The device of claim 12, wherein the wire ends include securing elements having a larger diameter than a diameter of the wire.

19. A method of removing tissue from a body, the method comprising:

inserting a collapsible bag through a surgical opening, the bag including an opening disposed at a first end and a closed bottom disposed at a second end opposite the opening, and a plurality of wires attached to and extending along an interior surface of the bag and having wire ends extending beyond the opening of the bag, wherein opposing ends of at least one wire have matching indicators to indicate opposing ends of the same wire, wherein the wires along the interior surface of the bag each intersect one another at a defined crossover point disposed at the second end of the bag;

inserting a tissue to be removed into the bag;

positioning the bag so that the bag opening and wire ends extend outside of the surgical opening while a remainder of the bag holding the tissue to be removed remains inside of the surgical opening;

after positioning the bag, routing the wire ends through a distal end of a tubular positioning member, the tubular positioning member being attached to a housing at a proximal end;

connecting the wire ends to a slotted wire retracting element, the wire retracting element being configured to securely receive the wire ends and being moveable relative to the housing to produce a pulling force on the wires; and moving the wire retracting element relative to the housing so as to pull the wires through the tubular positioning member to cause the wires to detach from the interior surface of the bag; and pulling the wires further so that the tissue contacts the distal end of the tubular positioning member and so that the wires move through the tissue to segment the tissue.

20. The method of claim 19, wherein multiple wires include indicators and wherein the indicators are sequentially labelled to indicate an overlay order of each wire.

* * * * *